US011020740B2

(12) United States Patent
Lee et al.

(10) Patent No.: US 11,020,740 B2
(45) Date of Patent: Jun. 1, 2021

(54) MICROFLUIDIC BIOCHIP WITH ENHANCED SENSITIVITY

(71) Applicant: New Jersey Institute of Technology, Newark, NJ (US)

(72) Inventors: Eon Soo Lee, Tenafly, NJ (US); Bharath Babu Nunna, Randolph, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 16/168,484

(22) Filed: Oct. 23, 2018

(65) Prior Publication Data

US 2019/0118178 A1 Apr. 25, 2019

Related U.S. Application Data

(60) Provisional application No. 62/576,208, filed on Oct. 24, 2017, provisional application No. 62/589,097, filed on Nov. 21, 2017.

(51) Int. Cl.
| | |
|---|---|
| *B01L 3/00* | (2006.01) |
| *G01N 27/22* | (2006.01) |
| *G01N 33/487* | (2006.01) |
| *G01N 33/53* | (2006.01) |
| *G01N 33/574* | (2006.01) |
| *C01B 32/158* | (2017.01) |
| *B82Y 30/00* | (2011.01) |
| *B82Y 15/00* | (2011.01) |

(52) U.S. Cl.
CPC ..... *B01L 3/502715* (2013.01); *B01L 3/50273* (2013.01); *B01L 3/502761* (2013.01); *G01N 27/226* (2013.01); *G01N 33/48707* (2013.01); *G01N 33/5304* (2013.01); *G01N 33/57488* (2013.01); *B01L 3/502746* (2013.01); *B01L 2200/027* (2013.01); *B01L 2300/023* (2013.01); *B01L 2300/0645* (2013.01); *B01L 2300/0819* (2013.01); *B01L 2300/0883* (2013.01); *B01L 2300/0896* (2013.01); *B01L 2300/12* (2013.01); *B01L 2300/161* (2013.01); *B01L 2400/0406* (2013.01); *B01L 2400/08* (2013.01); *B01L 2400/088* (2013.01); *B82Y 15/00* (2013.01); *B82Y 30/00* (2013.01); *C01B 32/158* (2017.08); *G01N 2800/7028* (2013.01)

(58) Field of Classification Search
CPC ......... B01L 3/502715; B01L 3/502761; B01L 2300/023; B01L 3/50273; B01L 2300/0645; B01L 2300/0819; B01L 2300/0896; B01L 2300/12; B01L 2300/161; B01L 2400/0406; B01L 2400/08; B01L 3/502746; B01L 2300/0883; B01L 2400/088; B01L 2200/02; G01N 27/226; G01N 33/48707; G01N 33/5304; G01N 33/57488; G01N 2800/7028; C01B 32/158; B82Y 30/00; B82Y 15/00
USPC ...................................................... 435/287.2
See application file for complete search history.

(56) References Cited

U.S. PATENT DOCUMENTS

| | | | |
|---|---|---|---|
| 6,319,469 B1 | 11/2001 | Mian et al. | |
| 6,709,869 B2 | 3/2004 | Mian et al. | |
| 7,087,148 B1* | 8/2006 | Blackburn | B82Y 30/00 204/403.06 |
| 8,354,307 B2* | 1/2013 | Lee | G01N 27/3276 422/50 |
| 9,234,867 B2* | 1/2016 | Briman | G01N 27/3278 |
| 9,897,608 B2* | 2/2018 | Huang | G01N 33/57449 |
| 10,481,154 B2 | 11/2019 | Lee et al. | |
| 2005/0084921 A1* | 4/2005 | Cranley | C12P 7/04 435/25 |
| 2005/0095698 A1* | 5/2005 | Carlson | G01N 21/6445 435/287.2 |
| 2005/0100937 A1* | 5/2005 | Holmes | A61B 5/14542 435/6.12 |
| 2005/0158704 A1 | 7/2005 | Tyvoll et al. | |
| 2006/0147344 A1* | 7/2006 | Ahn | G01N 27/44717 422/70 |

(Continued)

FOREIGN PATENT DOCUMENTS

| | | |
|---|---|---|
| CN | 1462878 A | 12/2003 |
| WO | 2017223205 A1 | 12/2017 |

OTHER PUBLICATIONS

"Technical Program for Monday, Nov. 9, 2015", NIH-IEEE 2015 Strategic Conference on Healthcare Innovations and Point-of-Care Technologies for Precision Medicine, Nov. 9-10, 2015, NIAID Conference Center, Bethesda, MD, 8 pages.

(Continued)

*Primary Examiner* — Ann Y Lam
(74) *Attorney, Agent, or Firm* — Lerner, David, Littenberg, Krumholz & Mentlik, LLP

(57) ABSTRACT

A microfluidic biochip for detecting disease antigens using gold nano interdigitated electrode circuit under a controlled self-driven flow condition is disclosed. The biochip incorporates hydrophilic microchannels for controlled self-driven flow and gold nano interdigitated electrodes for capacitive sensing with enhanced sensitivity. The biochip's microchannel has a surface treated with oxygen plasma to control microchannel surface hydrophilicity and flow rate of the biofluid sample. Carbon Nanotubes (CNTs) are utilized as an intermediate layer to enhance the binding capability to nano electrodes to enhance sensitivity. Due to the carboxylic groups of the CNTs, covalent bond binding between the antibodies and the CNTs allows the antibodies to adhere more readily on the surface of the electrodes. The quantity of antibodies attaching to the surface is increased due to the high surface to area ratio in CNTs.

19 Claims, 22 Drawing Sheets

(56) References Cited

U.S. PATENT DOCUMENTS

| | | | |
|---|---|---|---|
| 2006/0193748 A1* | 8/2006 | Tai | G01N 30/34 |
| | | | 422/70 |
| 2007/0116701 A1* | 5/2007 | Gurney | A61P 1/18 |
| | | | 424/143.1 |
| 2007/0122819 A1 | 5/2007 | Wu et al. | |
| 2008/0253929 A1* | 10/2008 | Park | B29C 59/14 |
| | | | 422/68.1 |
| 2009/0084686 A1* | 4/2009 | Yun | G01N 33/5438 |
| | | | 205/792 |
| 2010/0075340 A1 | 3/2010 | Javanmard et al. | |
| 2010/0273672 A1* | 10/2010 | Demoustier-Champagne | |
| | | | G01N 33/54373 |
| | | | 506/9 |
| 2011/0005932 A1 | 1/2011 | Jovanovich et al. | |
| 2014/0257047 A1* | 9/2014 | Sillay | A61B 5/4082 |
| | | | 600/301 |
| 2016/0099701 A1* | 4/2016 | Rinaldi | H03H 9/13 |
| | | | 422/90 |
| 2016/0169905 A1* | 6/2016 | Verschoor | G01N 33/5432 |
| | | | 435/7.1 |
| 2016/0299138 A1 | 10/2016 | Almasri et al. | |
| 2016/0303565 A1 | 10/2016 | Bhagat et al. | |
| 2017/0067889 A1* | 3/2017 | Tamir | G01N 27/4145 |
| 2018/0128823 A1* | 5/2018 | Lee | G01N 27/227 |
| 2018/0303386 A1* | 10/2018 | Hall | A61B 5/14539 |

OTHER PUBLICATIONS

Alcantar, et al., "Polyethylene Glycol-Coated Biocompatible Surfaces", Journal of Biomedical Materials Research: An Official Journal of the Society for Biomaterials, the Japanese Society for Biomaterials, and the Australian Society for Biomaterials and the Korean Society for Biomaterials, vol. 51, No. 3, Sep. 2000, pp. 343-351.

American Cancer Society. Cancer Facts & Figures 2017.Atlanta? American Cancer Society? 2017, 76 pages.

Ichikawa, et al., "Interface Motion of Capillary-Driven Flow in Rectrangular Microchannel", Journal of Colloid and Interface Science, vol. 280, No. 1, Dec. 2004, pp. 155-164.

Jokerst, et al., "Nano-Bio-Chips for High Performance Multiplexed Protein Detection: Determinations of Cancer Biomarkers in Serum and Saliva Using Quantum Dot Bioconjugate Labels", Biosensors and Bioelectronics, vol. 24, No. 12, Aug. 2009, pp. 3622-3629.

Lab-on-a-chip technology to help protect future space explorers and detect life forms on Mars, SpaceRef. 2017. Retrieved on Mar. 7, 2017 at http://www.spaceref.com/news/viewpr.html?pid=14312.

Lazcka, et al., "Pathogen Detection: A Perspective of Traditional Methods and Biosensors", Biosensors and Bioelectronics, vol. 22, No. 7, Feb. 2007, pp. 1205-1217.

Lucas, R., "Rate of Capillary Ascension of Liquids", Kolloid Z, vol. 23, No. 15, 1918, pp. 15-22.

Memarzadeh, Sanaz, "Five Facts About Ovarian Cancer Everyone Should Know", Newsroom, University of California, Los Angeles (UCLA), Health Sciences, Aug. 2018, 4 pages.

Munoz, Hector, "Detecting Ovarian Cancer with a Cell Phone and a Microfluidic Chip", Microfluidic Future, Oct. 2011, 8 pages.

Nunna, et al, "Innovative Point-of-Care (POC) Micro Biochip for Early Stage Ovarian Cancer Diagnostics", Sensors & Transducers, vol. 214, No. 7, Jul. 2017, 9 pages.

Nunna, et al., "Point-of-Care (POC) Micro Biochip for Cancer Diagnostics", InProceedings of the TechConnect World Innovation Conference and Expo 2017, May 2017, pp. 14-17.

Rusling, et al., "Measurement of Biomarker Proteins for Point-of-Care Early Detection and Monitoring of Cancer", Analyst, vol. 135, No. 10, Jul. 2010, pp. 2496-2511.

Shadfan, et al., "A Multiplexable, Microfluidic Platform for the Rapid Quantitation of a Biomarker Panel for Early Ovarian Cancer Detection at the Point-of-Care", Cancer Prevention Research, vol. 8, No. 1, Jan. 2015, 19 pages.

Washburn, Edward, "The Dynamics of Capillary Flow", Physical Review, vol. 17, No. 3, Mar. 1921, p. 273.

Whitesides, George, "The Origins and the Future of Microfluidics", Nature, vol. 442, No. 7101, Jul. 2006, p. 368.

Zhang, et al., "Microfluidics and Cancer: Are We There Yet?", Biomedical Microdevices, vol. 15, No. 4, Aug. 2013, pp. 595-609.

Nunna, et al., "Ovarian Cancer Diagnosis Using Micro Biochip", InNIH-IEEE 2015 Strategic Conference on Healthcare Innovations and Point-of-Care Technologies for Precision Medicine, Nov. 2015, pp. 9-10.

"Lab-on-a-chip technology to help protect future space explorers and detect life forms on Mars", SpaceRef, Press Release From: Marshall Space Flight Center (http://www.msfc.nasa.gov/), Posted: Tuesday, Jun. 1, 2004.

Alcantar et al., "Polyethylene glycol-coated biocompatible surfaces", Journal of Biomedical Materials Research, Jun. 2000, pp. 343-451.

Altintas et al., "A novel magnetic particle-modified electrochemical sensor for immunosensor applications", Sensors and Actuators B: Chemical, vol. 174, Nov. 2012, pp. 187-194.

Altintas et al., "Gold nanoparticle modified capacitive sensor platform for multiple marker detection", Talanta, vol. 118, Jan. 2014, pp. 270-276.

American Cancer Society, Cancer Facts & Figures 2017, Atlanta: American Cancer Society, 2017, pp. 1-76.

American Cancer Society, Survival Rates for Ovarian Cancer, American Cancer Society 2019, pp. 1-5.

Ayliffe et al., "Electric Impedance Spectroscopy Using Microchannels With Integrated Metal Electrodes", IEEE Journal of Microelectromechanical Systems, vol. 8, No. 1, Mar. 1999, pp. 50-57.

Balasubramanian, et al. "Biosensors based on carbon nanotubes", Analytical and Bioanalytical Chemistry, vol. 385, Issue 3, Jun. 2006, pp. 452-468.

Berggren et al., "Capacitive Biosensors", Journal of Electroanalysis, vol. 13, No. 3, Oct. 2000, pp. 173-180.

Buys et al., "Effect of Screening on Ovarian Cancer Mortality: The Prostate, Lung, Colorectal and Ovarian (PLCO) Cancer Screening Randomized Controlled Trial", Journal of American Medical Association, vol. 305, No. 22, Jun. 2011, pp. 2295-2303.

Calonge, Ned, "Screening for Ovarian Cancer: Recommendation Statement", Annals of Family Medicine, vol. 2, No. 3, May/Jun. 2004, pp. 260-262.

Chang et al., "Trace analysis of androgens and progestogens in environmental waters by ultra-performance liquid chromatography-electrospray tandem mass spectrometry", Journal of Chromatography A, vol. 1195, Apr. 2008, pp. 44-51.

Cramer et al., "Ovarian Cancer Biomarker Performance in Prostate, Lung, Colorectal, and Ovarian Cancer Screening Trial Specimens", American Association for Cancer Research, Mar. 2011, pp. 365-375.

Daniels et al., "Label-Free Impedance Biosensors: Opportunities and Challenges", National Institutes of Health, vol. 19, No. 12, May 16, 2007, pp. 1239-1257.

Das et al., "Protein Detection Using Arrayed Microsensor Chips: Tuning Sensor Footprint to Achieve Ultrasensitive Readout of CA-125 in Serum and Whole Blood", American Chemical Society, Analytical Chemistry, vol. 83, Jan. 18, 2011, pp. 1167-1172.

Diehl et al., "Hodgkin Lymphoma", Hematol Oncol Clin N Am 28 (2014) ix-x, Feb. 2014, pp. 1-2.

Gabriel et al., "The dielectric properties of biological tissues: I. Literature survey", Physics in Medicine & Biology, vol. 41, No. 11, Apr. 1996, pp. 2231-2249.

Gohagan et al., "The Prostate, Lung, Colorectal and Ovarian (PLCO) Cancer Screening Trial of the National Cancer Institute: History, Organization, and Status", Controlled Clinical Trials, vol. 21, Issue 6, Supplemental 1, Dec. 2000, pp. 251S-272S.

Grossman, David; "Screening for Ovarian Cancer US Preventive Services Task Force Recommendation Statement", Clinical Review & Education, American Medical Association, vol. 319, No. 6, Feb. 13, 2018, pp. 588-594.

(56) References Cited

OTHER PUBLICATIONS

Gómez-Sjöberg et al., "Impedance Microbiology-on-a-Chip: Microfluidic Bioprocessor for Rapid Detection of Bacterial Metabolism", Journal of Microelectromechanical Systems, vol. 14, No. 4, Aug. 2005, pp. 829-838.

Ichikawa et al., "Interface motion of capillary-driven flow in rectangular microchannel", Journal of Colloid and Interface Science, vol. 280, Issue 1, Dec. 2004, pp. 155-164.

Jacobs et al., "Review: Carbon nanotube based electrochemical sensors for biomolecules", Analytica Chimica Acta, vol. 662, Mar. 2010, pp. 105-127.

Jiang et al., "Gold-Labeled Nanoparticle-Based Immunoresonance Scattering Spectral Assay for Trace Apolipoprotein Al and Apolipoprotein B", Clinical Chemistry, vol. 52, No. 7, Jun. 2006, pp. 1389-1394.

Jiang et al., "Protein immobilization on carbon nanotubes via a two-step process of diimide-activated amidation", Journal of Materials Chemistry, vol. 14, Nov. 2003, pp. 37-39.

Kallempudi et al., "A nanostructured-nickel based interdigitated capacitive transducer for biosensor applications", Sensors and Actuators B: Chemical, vol. 160, Issue 1, Dec. 2011, pp. 891-898.

Kozak et al., "Characterization of serum biomarkers for detection of early stage ovarian cancer", Proteomics, vol. 5, Mar. 2005, pp. 4589-4596.

Kramer et al., "A National Cancer Institute Sponsored Screening Trial for Prostatic, Lung, Colorectal, and Ovarian Cancers", Cancer Supplement, vol. 71, No. 2, Jan. 1993, pp. 589-593.

Lazcka et al., "Pathogen detection: A perspective of traditional methods and biosensors", Biosensors and Bioelectronics, vol. 22, Issue 7, Feb. 2007, pp. 1205-1217.

Lu et al., "Ultrasensitive electrochemical immunosensor for HE4 based on rolling circle amplification", Biosensors and Bioelectronics, vol. 33, Jan. 16, 2012, pp. 216-221.

Mamishev et al., "Interdigital Sensors and Transducers", Proceedings of the IEEE, vol. 92, No. 5, May 2004, pp. 808-845.

Mok et al., "Prostasin, a Potential Serum Marker for Ovarian Cancer: Identification Through Microarray Technology", Journal of the National Cancer Institute, vol. 93, No. 19, Oct. 3, 2001, pp. 1458-1464.

Moore, et al., "The use of multiple novel tumor biomarkers for the detection of ovarian carcinoma in patients with a pelvic mass", Gynecologic Oncology, vol. 108, Issue 2, Feb. 2008, pp. 402-408.

NIH National Cancer Institute; Cancer Screening and Early Detection Research; Research Areas: Screening and Early Detection—National Cancer Institute, https://www.cancer.gov/research/areas/screening, Updated Dec. 19, 2018, pp. 1-5.

Nunna et al., "Biomolecular Detection using Molecularly Imprinted Polymers (MIPs) at Point-of-Care (POC) Micro Biochip", Ovarian Cancer Diagnosis using Micro Biochip, NIH-IEEE 2015 Strategic Conference on Healthcare Innovations & Point-of-Care Technologies for Precision Medicine, Nov. 9-10, 2015, p. 1.

Nunna et al., "Flow control mechanism of capillary driven flow in microchannel using non-mechanical forces", Bulletin of the American Physical Society, APS—69th Annual Meeting of the APS Division of Fluid Dynamics—Session Index DFD16, Nov. 2016, pp. 1-2 (Abstract Only included).

Nunna et al., "Influence on Capillary Flow of Human Blood in PDMS Micro Channels due to various Surface Treatments", Jul. 2016, Technical Presentation Only.

Nunna et al., "Innovative Point-of-Care (POC) Micro Biochip for Early Stage Ovarian Cancer Diagnostics", Sensors & Transducers, vol. 214, Issue 7, Jul. 2017, pp. 12-20.

Nunna, et al., "Point-of-Care (POC) Micro Biochip for Cancer Diagnostics", Id Innovation Conference and Expo 2017, May 2017, pp. 110-113.

Rusling, et al., "Measurement of Biomarker Proteins for Point-of-Care Early Detection and Monitoring of Cancer", Analyst, vol. 135, No. 10, Oct. 2010, pp. 2496-2511.

Sarojini et al., "Early Detection Biomarkers for Ovarian Cancer", Journal of Oncology, vol. 2012, Article ID 709049, Nov. 19, 2012, pp. 1-15.

Schummer et al., "Evaluation of ovarian cancer remission markers HE4, MMP7 and Mesothelin by comparison to the established marker CA125", Gynecol Oncology, vol. 125, No. 1, Apr. 2012, pp. 1-12.

Siegel et al., "Colorectal Cancer Statistics, 2017", CA: A Cancer Journal for Clinicians, vol. 67, No. 3, May/Jun. 2017, pp. 177-193.

Soper et al., "Point-of-care biosensor systems for cancer diagnostics/prognostics", Biosensors and Bioelectronics, vol. 21, Issue 10, Apr. 15, 2006, pp. 1932-1942.

Su et al., "Ferrocenemonocarboxylic-HRP@Pt nanoparticles labeled RCA for multiple amplification of electro-immunosensing", Biosensors and Bioelectronics, vol. 26, May 6, 2011, pp. 4601-4604.

Tcherkassova, et al., "Combination of CA125 and RECAF biomarkers for early detection of ovarian cancer", Tumor Biology, vol. 32, May 28, 2011, pp. 831-838.

Tsouti et al., "Capacitive microsystems for biological sensing", Biosensors and Bioelectronics, vol. 27, May 2011, pp. 1-11.

Wang et al., "Solubilization of Carbon Nanotubes by Nafion toward the Preparation of Amperometric Biosensors", Journal of American Chemical Society, vol. 125, No. 9, Feb. 2003, pp. 2408-2409.

Wang, Joseph "Electrochemical biosensors: Towards point-of-care cancer diagnostics", Biosensors and Bioelectronics, vol. 21, Issue 10, Apr. 2006, pp. 1887-1892.

Waxman, Alan; "Guidelines for Cervical Cancer Screening: History and Scientific Rationale", Clinical Obstetrics and Gynecology, vol. 48, No. 1, Mar. 2005, pp. 77-97.

Whitesides, George, "The Origins and the Future of Microfluidics", Nature, vol. 442, Jul. 2006, pp. 368-373.

World Ovarian Cancer Day, About Ovarian Cancer, World Ovarian Cancer Day 2019, pp. 1-5, https://ovariancancerday.org/what-is-ovarian-cancer/.

Zhu et al., "Electrochemical Determination of Reversible Redox Species At Interdigitated Array Micro/Nanoelectrodes Using Charge Injection Method", IEEE Transactions on Nanobioscience, vol. 4, No. 2, Jun. 2005, pp. 164-169.

Zhuang et al., "New Nitrogen-Doped Graphene/MOF-modified catalyst for Fuel Cell Systems", The Electrochemical Society ECS Transactions, vol. 72 (8), Jun. 1, 2016, pp. 149-154.

Zhuang et al., "Synthesis of Nitrogen-Doped Graphene Catalyst by High-Energy Wet Ball Milling for Electrochemical Systems", International Journal of Energy Research, Jun. 12, 2016, pp. 1-14.

American Cancer Society, "Cancer Facts and Figures 2016," copyrighted 2016, American cancer Society Inc., Atlanta, Ga.; 72 pages.

Carrara S, Bhalla V, Stagni C, Benini L, Ferretti A, Valle F, Gallotta A, Riccò B, Samorì B. Label-free cancer markers detection by capacitance biochip. Sensors and Actuators B: Chemical. Feb. 2, 2009;136(1):163-72.

Dimaki et al., "A Compact Microelectrode Array Chip With Multiple Measuring Sites For Electrochemical Applications", Sensors (Basel), May 2014, vol. 14 No. 6, pp. 9505-9521.

Eddington DT, Puccinelli JP, Beebe DJ. Thermal aging and reduced hydrophobic recovery of polydimethylsiloxane. Sensors and Actuators B: Chemical. Mar. 30, 2006;114(1):170-2.

Ginn BT, Steinbock O. Polymer surface modification using microwave-oven-generated plasma. Langmuir. Sep. 16, 2003;19(19):8117-8.

Hrncír E, Rosina J. Surface tension of blood. Physiol Res. Jan. 1997;46:319-21.

International Application Status Report for Application No. PCT/US2018/018316 dated Mar. 1, 2018, 2 pages.

International Search Report from Application No. PCT/US18/18316, dated Jun. 15, 2018.

Laczka O, Baldrich E, Mun~oz FX, del Campo FJ. Detection of *Escherichia coli* and *Salmonella typhimurium* using interdigitated microelectrode capacitive immunosensors: the importance of transducer geometry. Analytical chemistry. Oct. 1, 2008;80(19):7239-47.

Lamour G, Hamraoui A, Buvailo A, Xing Y, Keuleyan S, Prakash V, Eftekhari-Bafrooei A, Borguet E. Contact angle measurements using a simplified experimental setup. Journal of chemical education. Dec. 1, 2010;87(12)1403-7.

(56) References Cited

OTHER PUBLICATIONS

Limbut W, Kanatharana P, Mattiasson B, Asawatreratanakul P, Thavarungkul P. A comparative study of capacitive immunosensors based on self-assembled monolayers formed from thiourea, thioctic acid, and 3-mercaptopropionic acid. Biosensors and Bioelectronics. Aug. 15, 2006;22(2):233-40.

Nunna BB, Zhuang S, Lee ES. Hemorheology in PDMS micro channel with varied surface roughness. APS. Nov. 2015.

Nunna BB, Zhuang S, Lee ES. Squeeze flow with capillary effect in Nano Imprint Lithography (NIL) process. APS. Nov. 2015.

Tan SH, Nguyen NT, Chua YC, Kang TG. Oxygen plasma treatment for reducing hydrophobicity of a sealed polydimethylsiloxane microchannel. Biomicrofluidics. Sep. 30, 2010;4(3):032204, 9 pages.

Tsouti V, Boutopoulos C, Zergioti I, Chatzandroulis S. Capacitive microsystems for biological sensing. Biosensors and Bioelectronics. Sep. 15, 2011;27(1):1-1.

Van Gerwen P, Laureyn W, Laureys W, Huyberechts G, De Beeck MO, Baert K, Suls J, Sansen W, Jacobs P, Hermans L, Mertens R. Nanoscaled interdigitated electrode arrays for biochemical sensors. Sensors and Actuators B: Chemical. Jun. 25, 1998;49(1-2):73-80.

Washburn, Edward, "The Dynamics of Capillary Flow", Physical Review, vol. 17, No. 3, Mar. 1921, pp. 273-283.

Xiao D, Zhang H, Wirth M. Chemical modification of the surface of poly (dimethylsiloxane) by atom-transfer radical polymerization of acrylamide. Langmuir. Dec. 10, 2002;18(25):9971-6.

Yi M, Jeong KH, Lee LP. Theoretical and experimental study towards a nanogap dielectric biosensor. Biosensors and Bioelectronics. Jan. 15, 2005;20(7):1320-6.

\* cited by examiner

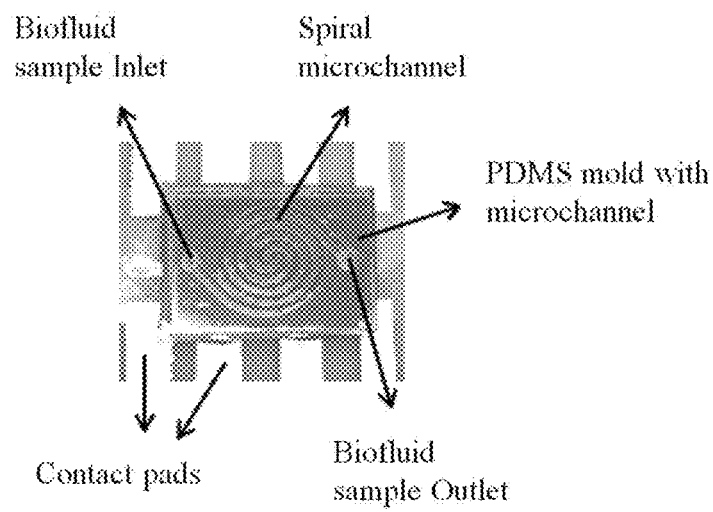
FIG. 1.
 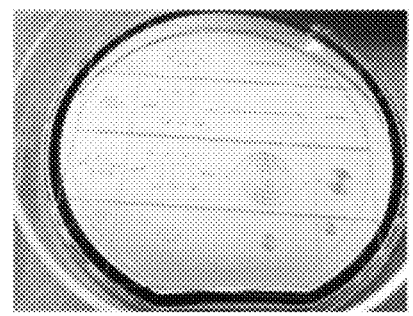
FIG. 2A  FIG. 2B
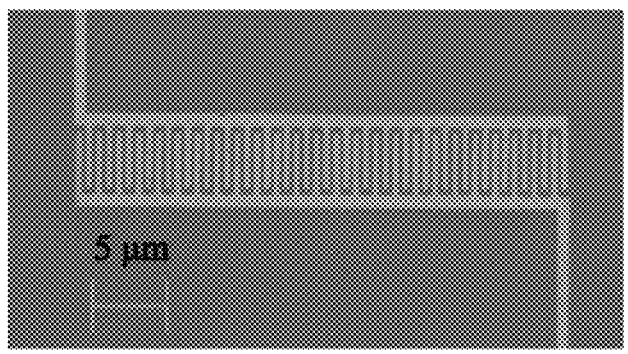 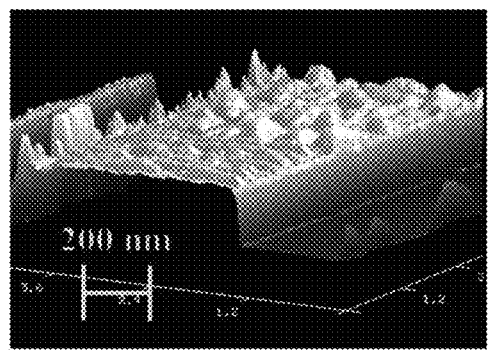
FIG. 3A  FIG. 3B

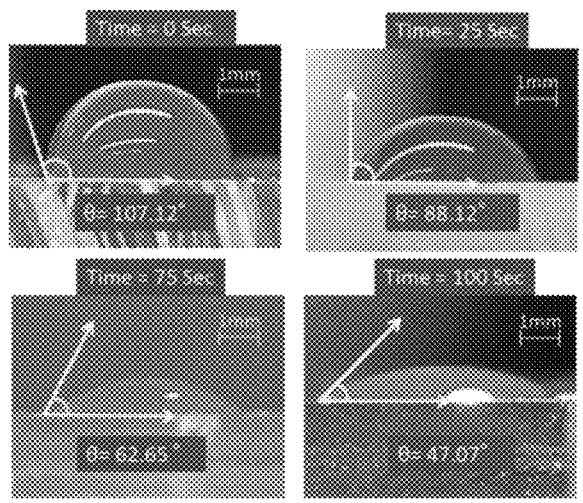
FIGS. 6A-D
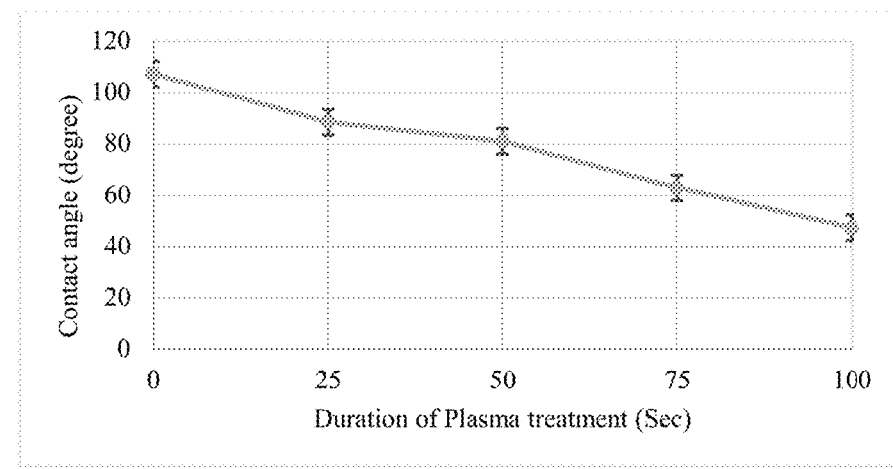
Fig-7.

| Ovarian Disease (OVC) Biomarkers | Threshold | Limit of Detection | Sensitivity | Specificity |
|---|---|---|---|---|
| CA-125 | 36 U/mL [10] | 0.1 U/mL [17] | 15% (at stage 1)  50% (at all stages) [12] | 95%[12] |
| HE-4 | 44 pmol/L (premenopausal)  62 pmol/L (postmenopausal) [11] | 0.06 pmol/mL [18] | 40% (at stage 1)  76% (at all stages) [12]* | 95% [12]* |
| RECAF | 7500 U/mL [10] | 1.7 pg/mL [16] | 75% (at stage 1-2)  83% (at all stages) [12]* | 100% [10]* |
| Prostasin | 7.5 ug/mL [13] | - | 92% (at all stages) [13]* | 94%[13]* |
| Apo A-1 | 0.8 mg/mL (Anything below this limit is considered as OVC)[14] | 2.04 ug/L [19] | 93.9% (at stage 1-2)  91.6% (at stage 3-4) [15]** | 95% [15]** |
| TTR | 150 ug/mL (Anything below this limit is considered as OVC) [14] | 0.1 ng/L [20] | 93.9% (at stage 1-2)  91.6% (at stage 3-4) [13]** | 95% [16]** |

*Biomarker used in conjunction with CA-125 for specificity and sensitivity measurements

**Biomarker used in conjunction with CA-125 and Apo A-1 and TTR for specificity and sensitivity measurements

FIG. 15

FIG. 39A
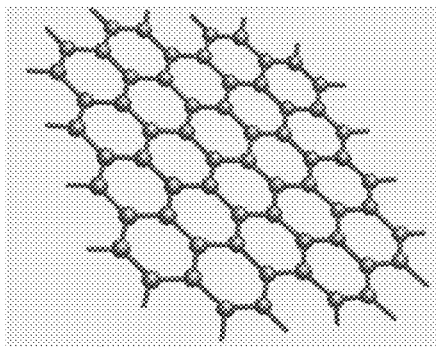
FIG. 39B
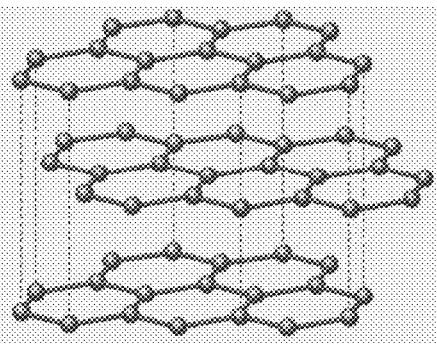
FIG. 39C
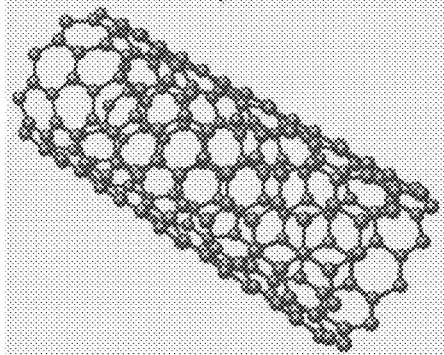
FIG. 39D
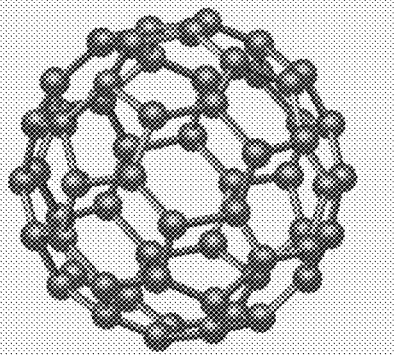
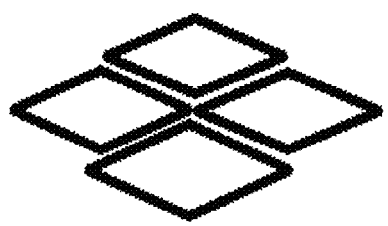
Graphene Oxide
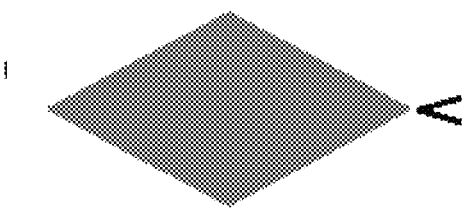
Nitrogen doped-Graphene
FIG. 40A
FIG. 40B pyrrolic N pyridinic N Graphitic (Substitutional) Nitrogen pyridinic⁺N–O⁻

MICROFLUIDIC BIOCHIP WITH ENHANCED SENSITIVITY

CROSS-REFERENCE TO RELATED APPLICATIONS

The present application claims the benefit of the filing date of U.S. Provisional Patent Application No. 62/576,208 filed on Oct. 24, 2017, and U.S. Provisional Patent Application No. 62/589,097 filed on Nov. 21, 2017 the disclosures of which are hereby incorporated herein by reference.

FIELD OF USE

This disclosure relates to a micro biochip for detecting disease antigens by using interdigitated electrodes, and allows enhanced sensitivity in biosensing using the carbon nanotubes. More particularly, it relates to a novel way of detecting disease-specific antigens using gold nano interdigitated electrodes and carbon nanotubes in a controlled self-driven flow.

BACKGROUND

Early detection of a disease can improve patient treatment outcomes that help to save lives and also reduce patient treatment expenses significantly. Most diseases, such as cancer, are curable when they are detected in their early stages. For example, the survival rate for ovarian cancer varies significantly depending on the stage at which the disease is diagnosed. With technologies currently in use, 85% of ovarian cancer cases are detected at advanced stages, at which the survival rate is 31%. Only 15% of the ovarian cancer cases are detected at early stages (stages 1A & 1B) at which the survival rate is 93%. Improvements in the ease with which the disease diagnosis process can be performed would lead to more frequent self-evaluations in which patients would have a much higher chance of having an earlier diagnosis. This in turn would help to enhance treatment outcomes.

Biochips are one technology currently under study to improve disease diagnosis. Biochips are defined as devices on which biomolecules such as DNA, proteins, sugar chains and cells containing these biomolecules are fixed in a large number, termed DNA, protein, glycochips and cell chips, respectively. Target molecules and compounds may interact with biomolecules on these chips that when analyzed may detect a disease state. However, the current state of the art biochips have many drawbacks. For example, diagnosis including screening and monitoring in the early phase after onset is difficult with current health check-up sensitivity and specificity. There is still a need to detect diseases such as cancers, lifestyle-related diseases such as hypertension and diabetes, and infectious diseases including influenza, rapidly, simply and accurately at a low cost using one drop of blood or test sample. Furthermore some biochips lack the ability to utilize other patient samples other than blood, for example other bodily fluids such as urine, saliva, spinal fluid, and the like. Also, some biochips are manufactured with glass that causes problems due to etching of the glass, cost of manufacturing, and extreme limitation of biochip construction. Use of other materials such as polymer based materials has failed due to the hydrophobic nature of the polymer material and its tendency for reducing the flow of any fluid.

The ability of point-of-care (POC) systems to detect several biomarkers as varied biosensor arrays leads to personalized therapies and continuous monitoring of treatment of the disease. However, there is still a large need for growth in their performance rating. For example, noise reduction is further needed in the detection signal. Some have suggested space confinement between interdigitated electrodes in the nanoscale to help minimize the noise from the detection signal. However there are still many drawbacks to such space confinement methods including reduction of space to place antigen detectors.

Carbon nanotubes (CNTs) have attracted some attention in recent years due to their ultra-high specific surface area and outstanding electrical, mechanical and electrochemical properties. CNTs due to their large length-to-diameter aspect ratios provides high surface to volume ratio, which enables them to obtain high ultra fast detection of biological species even at low concentration. The CNTs in the field of biosensing have advantages like better electron-transfer for sensing activity, higher stability and longer durability. Additional to this, functionalized CNTs can be used to attach or bind any desired chemical species for enhancing the solubility and biocompatibility of the tubes. Although CNTs are very good for biosensing, their applications on interdigitated electrodes based capacitive biosensor under shear flow rate conditions have been met with difficulties and no success.

Thus, although biochip technology holds great potential for use in health monitoring systems around the world, and in particular in remote areas, there remain significant areas for improvement in the performance and ease of use of such technology. Complex disease diagnostics such as cancer diagnostics is still a nascent area of research that has not been completely explored by biochip researchers. There is also a need in the art to understand the sensitivity of the CNTs based sensor under dynamic conditions of analytes on top of a sensor surface, and optimize stability and functionality of CNTs based sensor when antigens, such as but not limited to the CA-125 cancer antigens, passes through an integrated microfluidic channel.

BRIEF SUMMARY

This innovation primarily intended to the field of complex diseases diagnosis, by detecting the disease antigen using a gold nano interdigitated electrode circuit under a controlled self-driven flow condition in a microfluidic biochip. Depending on the implementation there may be one or more nano interdigitated electrode circuits in the microfluidic biochip. Disease diagnosis is still tedious and expensive in the majority of the cases. The proposed biochip replaces complex disease diagnosis process with the implementation of a Point-of Care (POC) biochip. Early detection of the disease can enhance the preventive measures, increase curability of the disease, reduce health care costs, and finally, improve the quality of life for patients. To successfully detect the disease-specific antigen (like CA-125 a prominent cancer antigen), the biochip incorporates hydrophilic microchannels for controlled self-driven flow and gold nano interdigitated electrodes for capacitive sensing with enhanced sensitivity. There may be one or more microchannels depending on the implementation of the microfluidic biochip. The biofluid sample flow in microchannels is self-driven due to the capillary effect of the biofluid in the hydrophilic microchannels. Therefore no pumps are needed. The microchannel in the biochip is surface treated with oxygen plasma, for example, to control the hydrophilicity of the microchannel surface which in turn controls the flow rate of biofluid in the microchannel. There may be other methods to alter the hydrophilicity, for example, using micro patterning methods on the surface of the microchannel. Gold nano interdigitated electrode circuit is fabricated on the surface of the microchannel to detect the biomolecular interactions in the microchannel. When the biofluid sample with CA-125 antigens, is self-driven in the microchannel, the CA-125 antigens from the biofluid form an antigen/antibody conjugations with the CA-125 antibodies that are immobilized on the Surface-activated SAM layer of the gold nano interdigitated electrodes. This antigen/antibody conjugation is detected via the change in the capacitance of the uniquely designed nano circuit in the biochip. Detection of CA-125 antigen from a biofluid sample using the gold nano interdigitated electrodes in a microfluidic channel under a controlled self-driven flow condition is thus accomplished.

The insulation on top of the gold interdigitated electrodes is critical, in order to avoid the chances of short circuit and minimize the noise. Self-Assembled Monolayer (SAM) primarily helps to provide proper insulation. SAM layer forms significantly better adhesion on top of gold when compared to any other oxides or semiconductors. CA-125, a prominent cancer antibody, is used as an example; however the principles of this invention may be utilized with other antigens/antibody pairs to detect other diseases from a biofluid sample including, but not limited, to biomarkers like kallikreins (KLK6 & KLK7) which are highly active at the earlier stages of the diseases like ovarian cancer.

The self-driven flow in the microchannel is also controlled by altering the contact angle. The contact angle is varied by various surface treatments to the PDMS microchannel. The controlled flow rate of biofluid with targeted biomolecules in microchannels helps to form the antigen/antibody conjugation in microchannel. When the biofluid sample is self-driven in the microchannel, the targeted biomolecules from the biofluid form biomolecular interactions with the corresponding biomolecules that are immobilized on the gold nano interdigitated electrodes. Again, biomolecular interactions are detected via the change in the capacitance of the uniquely designed nano circuit in the biochip. Thus the change in electrical properties of the circuit helps to detect the biomolecular interactions.

Possible uses of the biochip further include, but are not limited to, lab on the chip technology, point of care devices, point of screening devices, and detection of drug effectiveness. One novelty of the technology is the enhanced detection of the antigen/antibody interaction under shear flow condition. The biofluid sample is self-driven in the microchannel by itself without any external devices. The flow rate of the biofluid sample flow can be controlled without any external flow control devices. The blood plasma can be separated from the whole blood during the flow in the microchannel. Enhanced sensitivity with the enhancement of the immobilized antibody intensity on the sensing region of the biochip is accomplished.

Depending on the embodiments, possible variations within the scope of this invention include, but are not limited to, having the biochip circuit fabricated with any conducting material other than gold, such as but not limited to other metals or alloys having sufficient conductivity properties for this biochip application. Other variations include, but are not limited to, using the biochip with biomolecules of any type which flow in biofluid. The microchannel size can also vary depending on the implementation. The interdigitated electrodes (IDE) size may also vary depending on application. One or more interdigitated electrodes may be utilized.

The microfluidic chip and accompanying composition also allows enhanced sensitivity in biosensing using the carbon nanotubes. Detection of targeted biomolecules from a biofluid sample is accomplished under a controlled self-driven flow condition in a microchannel using gold nano interdigitated electrodes and carbon nanotubes.

The composition and apparatus successfully detect a disease-specific antigen, a biochip. The biochip incorporates hydrophilic microchannels for controlled self-driven flow and gold nano interdigitated electrodes for capacitive sensing with enhanced sensitivity. A biofluid sample flows in microchannels and is self-driven due to a capillary effect of the biofluid in the hydrophilic microchannels. The microchannel in the biochip is surface treated with oxygen plasma, for example, to control the hydrophilicity of the microchannel surface which in turn controls the flow rate of biofluid in the microchannel. Other methods to alter hydrophilicity may be used such as, but not limited to, using micro patterning methods on the surface of the microchannel.

When the biofluid sample with disease antigens, is self-driven in the microchannel, the disease antigens from the biofluid form an antigen/antibody conjugations with the immobilized antibodies on the surface-activated (SAM) layer of the gold nano interdigitated electrodes. This antigen/antibody conjugation is detected via a change in the capacitance of the uniquely designed nano circuit in the biochip. A CNT based biosensor is compared with a non-CNT based biosensor for checking enhancement in sensitivity when using the CNT based biosensor. Depending on the implementation nanoparticles may be made from either metallic materials, including but not limited to, gold (AU) and/or silver (Ag), or non-metallic carbon materials including carbon nanotubes (CNT), graphenes, or active carbons may be utilized. Furthermore, nanoparticles may be selected from a group consisting of a metallic material, a gold (Au) material, a silver (Ag) material, a non-metallic carbon material, a carbon nanotube (CNT), a graphene, an active carbon, and any combination thereof.

Depending on the embodiment, a non-Carbon nanotube (CNT) based biosensor consists of antibodies immobilized on top of the SAM layer using glutaraldehyde. CA-125 antibodies are bonded covalently with the CNTs to provide more stability of the antibodies even under shear flow rate conditions. The increased percentage of the carboxylic functionalized group on the surface of the CNTs provides a platform to attach more antibodies, which would directly influence in a positive fashion stability and sensitivity.

Carbon nanotubes (CNTs) are also used as an intermediate layer to enhance the binding capability to the nano electrodes to enhance the sensitivity. Due to carboxylic groups of the CNTs, binding is with a covalent bond between the antibodies and the CNTs. The quantity of antibodies attaching to the surface is increased due to high surface to area in CNTs. Enhanced sensitivity is furthered with using the covalent bond between the antibodies and the sensing electrodes. Enhanced sensitivity is also furthered using enhancement of the immobilized antibody intensity on the sensing region of the biochip.

Unlike prior devices and methods, this device and composition utilizes detection of the biomolecules in the nano and sub nano scale size. The detection can also be in pico and femto scale concentration. Furthermore, unlike the prior art device, detection can be performed when the fluid is in motion in a microchannel where the biofluid is self-driven in microchannel using capillary action.

Possible variations of the invention include, but are not limited to, the CNTs changed with different carboxylic groups and percentages of such groups so that the binding of antibodies can be increased. The density of the CNTs may also be altered to increase sensitivity.

Further inventive objects include but are not limited to the following. The invention contemplates attaching CNTs (carbon nanotubes) on the surface of the electrodes to enhance the binding capability of the antibodies to the electrodes and also to increase the quantity of CNTs attached to electrodes. With enhanced binding of antibodies, the antibodies can sustain the shear flow of the fluid in the microchannel and assist in detecting antigens with a higher sensitivity. The invention has numerous applications for example, a lab on chip technology, point of care devices, point of screening devices, and detection of drug effectiveness.

The above objects and advantages are met by the present invention. In addition the above and yet other objects and advantages of the present invention will become apparent from the hereinafter-set forth Brief Description of the Drawings, Detailed Description of the Invention and claims appended herewith. These features and other features are described and shown in the following drawings and detailed description.

BRIEF DESCRIPTION OF THE DRAWINGS

The present invention will be better understood on reading the following detailed description of non-limiting embodiments thereof, and on examining the accompanying drawings, in which:

FIG. 1 illustrates a microfluidic biochip with spiral microchannel and nano interdigitated circuit;

FIGS. 2A and 2B illustrate a Si wafer after the photolithography process (channels formed from photo resist) as shown in FIG. 2A-Left and Si wafer after the dry etching process with microchannels of height 107 um as shown in 2B-Right.

FIGS. 3A and 3B illustrate microscopic images, FIG. 3A shows the microscopic image of the gold interdigitated electrodes fabricated on the Si wafer (Left) and FIG. 3B shows gold electrodes with SAM layer (Thiourea) (Right);

FIGS. 6A-D illustrate images of Sessile blood drop (4.2 ul volume) on PDMS surface treated with oxygen plasma for various durations (0 sec, 25 sec, 75 sec, & 100 sec);

FIG. 7 illustrates a plot of contact angle made by drops on PDMS surfaces treated with oxygen plasma for various durations (0 sec, 25 sec, 75 sec, & 100 sec);

FIG. 10A is a schematic of an electrode with active 'Top' and 'Side' surfaces of the electrode as shown in (FIG. 9) and FIG. 10B is the equivalent circuit model of (FIG. 10A) with single surface model for both Top and Side surfaces;

FIG. 15 illustrates a chart showing specificity and sensitivity of early detection ovarian disease biomarkers from various studies;

FIG. 24A illustrates a Point-of-Care (POC) Biochip as USB device and FIG. 24B illustrates a Point-of-Care (POC) Biochip as IOT device;

FIGS. 39A-39D illustrate additional carbon-based nanomaterials for nano electrodes, for example, left to right and top to bottom 39A graphene, 39B graphite, 39C carbon nanotube, and 39D fullerene;

FIGS. 40A-40B illustrate additional carbon based nanomaterials for nanoelectrodes.

DETAILED DESCRIPTION

Figure 4:
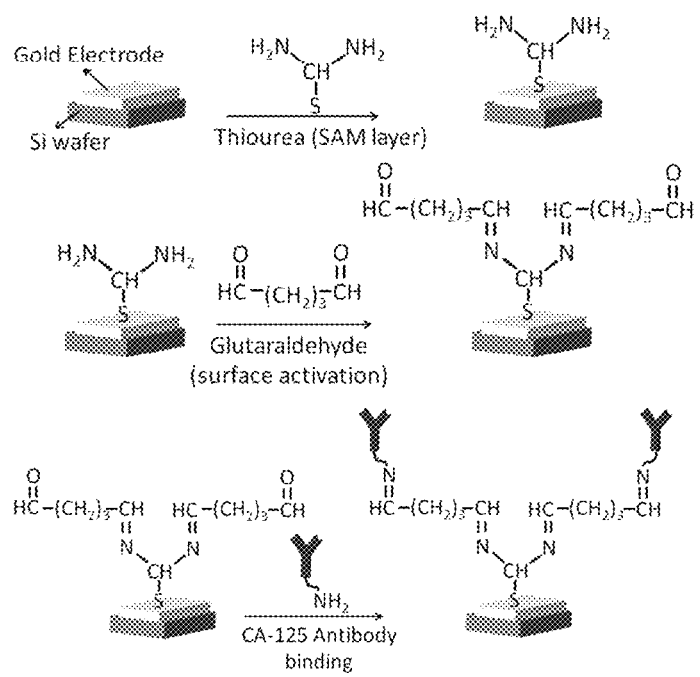
FIG. 4 illustrates a schematic representation of CA-125 antibody immobilization on nano gold interdigitated electrodes using the Surface-activated SAM layer.

In general, the invention overcomes the disadvantages of past attempts to detect disease-specific antigens. As used herein, "sample" refers to a sample from a mammalian patient. Non-limiting examples of a sample include, but are not limited to, tissue or bodily fluids. Bodily fluids can include blood, urine, saliva, spinal fluid, any combination of these, or any other fluid originating in the body. Where blood is referenced specifically, it is referred to merely for illustrative purposes and is in no way meant to limit the scope of the invention.

In a first aspect, the present invention relates to a point of care (hereinafter "POC") micro biochip. The terms "POC micro biochip," "microfluidic chip," "microfluidic biochip," "biochip," and "biosensor" are used interchangeably herein. The biochip includes at least one hydrophilic microchannel designed so that a sample, such as a blood sample, flows through the microchannel without assistance from any external devices. The biochip also includes at least one electrical property sensing mechanism in the form of gold nano interdigitated electrodes (hereinafter "IDE") on the surface of the microchannel. As referenced herein, an IDE may refer to a pair of electrodes, i.e., positive and negative, at a single location on the biochip. The components of the IDEs are discussed in greater detail below. The electrical property detected can be capacitance, impedance, resistance or voltage, for example. By sensing changes in the electrical property at the electrodes, a complex formation of an antigen (Ag) and antibody (AB) can be detected. The biochip further includes an inlet and outlet. The inlet is designed so that any microchannel structure on the biochip originates at the inlet, whether there are one, two, three or more microchannels. The inlet provides a depository location for the sample being tested. Similarly, the outlet is located at an opposite end of the microchannel from the inlet, and represents a point of departure for the sample from the biochip.

Referring to the biochip of FIG. 1, shown is a microfluidic biochip with spiral microchannel and nano IDE circuit. The biochip has a surface treated microchannel to control the self-driven flow in the microchannel. The microfluidic biochip incorporates the surface treated microchannels to facilitate a biofluid sample to flow without any need of external devices and the nano interdigitated circuit to sense the nano scale biological reactions. FIG. 1 is used as an example of the microfluidic biochip fabricated and utilized to generate the test results discussed herein. The biochip is incorporated with the spiral microchannel of 200 μm width and 107 μm depth and nano gold interdigitated circuit. Again these dimensions and the material of metal may be changed depending on the application. The fabrication steps and the functionality of the microchannels and nano circuit are explained in detail herein.

The biochip incorporates microchannels in order to serve the following criteria: (1) to control the self-driven flow of biofluid sample in the microchannel with no external flow control devices; (2) to minimize the sample volume requirement to micro level; and (3) to enhance the interaction between biofluid and the sensing mechanism with high surface area to volume ratio. Minimizing the external flow control device requirement reduces the contamination of the biofluid sample. When the biofluid comes in contact with the micro capillary channel, the surface tension of the biofluid draws the drop into the microchannel and induces the fluid into motion. The capillary flow is generated due to characteristics of the surface of the microchannel and its interaction with the fluid. The surface tension quantifies the capillary phenomena where the surface tension is the tensile force attained by the interface due to the imbalance of the cohesive forces of the molecules on the interface and the inner molecules of the fluid. The adhesion force (attraction force between the solid and liquid molecules) of biofluid with the surface of the microchannel causes the forward force at the edges. The surface tension will hold the surface intact and induce the whole liquid surface to move forward instead of moving only at the edges. The primary steps involved in the fabrication of hydrophilic polydimethylsiloxane (PDMS) microchannel are fabrication of PDMS microchannels and surface treatment of PDMS (hydrophobic to hydrophilic) that will now both be described.

Fabrication of the PDMS microchannels for the experiments disclosed herein included the following. Again these are merely given as examples and in no way meant to limit the scope of the invention.

Silicon wafers with microchannels were fabricated at the Center for Functional Nano materials at Brookhaven National Laboratory, Upton, N.Y. A silicon wafer of 4 inch diameter and 1 mm thickness was used to fabricate the microchannels on it. An ample Si-wafer thickness (1 mm) is chosen, since the channel structures are etched from Si wafer which are 100 um to 200 um height. The Silicon Wafer of 4-inch diameter was cleaned with acetone, isopropanol alcohol and deionized (DI) water. The wafer was dehydrated at 115° C. for about a minute using a hot plate and later allowed to reach the room temperature.

A positive photoresist (SPRTM 955) was deposited on top of the wafer. The positive photoresist was used to remove the material other than the channel area. The Si wafer, was coated with photoresist, placed on a spin coater and rotated at 1200 rpm for one minute to achieve the required thickness of photoresist on the wafer. The photoresist coated Si-wafer was placed on the UV light exposure tool (Karl Suss MABA6) and exposed to UV rays for 14 seconds. Due to UV exposure, the area not covered by the mask became soft. The wafer needed to be treated with CD-26 chemical and DI water to remove the photoresist remaining on the wafer on the UV exposed area. A Deep Reactive Ion Etching (DRIE), also called the Bosch process was used to etch a depth of 107 um. Areas not covered by the photoresist were etched from the Si wafer. Microchannels of height 107 um as shown in FIG. 2 were formed on the Si wafer.

A PDMS base was blended with a curing agent in definite proportion (1:10). Thorough mixing of solution was needed to make sure that the curing agent was uniformly distributed. Degassing was performed multiple times so that all the air bubbles trapped in the PDMS mixture were removed. The PDMS was cured at 100° C. for 35 minutes. When PDMS was cured, application of a steady pressure should help peel off the PDMS from Si wafer mold. A micro hole punching machine (Central Machinery, 5-Speed bench drill press) was used to make holes in the PDMS mold to create the inlet and outlet for the microchannels.

Surface treatment of the PDMS wafer to control the flow in the microchannel of the biochip included the following steps. Again, this is merely given as an example of the principles of the invention, and not intended to limit the scope of the invention to a particular embodiment.

PDMS (polydimethylsiloxane) is hydrophobic by nature and has a contact angle greater than 90 degrees. It resists the wettability of fluid on the surface. For the liquid to flow, a hydrophilic surface whose contact angle is less than 90 degrees was required. The hydrophobicity of the PDMS can be altered by performing various surface treatments like active group attachments (Israelachvili et al 2000), oxygen plasma treatment (Ginn et al 2003), chemical coating (Xiao et al 2002), and thermal aging (Eddington et al 2006).

In the present example given, the oxygen plasma treatment was used to convert hydrophobic nature of PDMS to hydrophilic nature. The hydrophilicity attained by surface treatment was sustained depending on factors like the temperature and humidity of the environment in which the PDMS mold was preserved. The oxygen plasma treatment of the PDMS introduces polar functional groups such as the Silanol groups (SiOH) on the surface of the PDMS. The silanol groups are responsible for converting the PDMS property from hydrophobic to hydrophilic. The oxygen plasma treatment also helps in increasing the adhesion property of the PDMS, so that it can be easily bonded with other substrates. However, the surface treatment due to oxygen plasma treatment is not permanent. PDMS regains its hydrophobicity after a certain period that is approximately 6 hours.

Example I

The primary steps involved in the fabrication of gold nano interdigitated electrodes were fabrication of gold nano interdigitated electrode (IDE) circuit and CA-125 Antibody immobilization on Electrodes. These steps are further described below. Again, these examples are given merely to explain the principles of the invention and are not meant to limit the scope of the invention to any particular embodiment.

For fabrication of the gold nano interdigitated electrode circuit (IDE) the silicon wafer was cut as per the dimensions desired and cleaned with isopropanol before starting the electrode fabrication. The Silicon wafer was then spin coated with positive tone photoresist. The photoresist used was PMMA-A6. The desired thickness of electrodes is 100 nm. The soft baking of the Silicon wafer was performed on a hot plate at around 180° C. for 120 seconds. The dimensions of the interdigitated electrodes fabricated were 500 nm width, 300 nm spacing (between the fingers) and 100 nm height as shown in FIG. 3A.

Electron beam Lithography (EBL) procedure was used to develop the pattern of nano interdigitated electrodes as per the CAD model of the interdigitated electrodes. The patterned Si wafer is then developed with MIBK: IPA for 60 s and washed with IPA for another 60 s and then dried with Nitrogen gas. A layer of Titanium of approximately 10 nm was deposited on the patterned grooves of the Si wafer using the Physical Vapor Deposition (Kurt J. Lesker PVD-75 Evaporator). Deposition of Titanium was for the improvement of the adhesion of gold on Silicon wafer. An approximately 90 nm of gold was deposited on top of the Si wafer. The lift-off process was performed by removing the positive tone photoresist using Acetone Ultrasonic bath for 3 minutes. The Si wafer with gold nano electrodes was then rinsed with distilled water and dried with Nitrogen gas.

FIG. 3A is the microscopic image of the nano interdigitated electrode and FIG. 3B is the atomic force microscopic image of gold nano electrode with the Self-assembled monolayer (SAM).

The CA-125 Antibody immobilization was accomplished on the electrodes as follows. The gold nano electrodes are electrically insulated using the SAM (Self-assembled monolayer) and then coated with antibodies. The electrodes are immersed in a 50 mM Thiourea solution ($CH_4N_2S$) for 12 hours to form the SAM layer (Self-assembled Monolayer) as shown in the FIG. 3b. To remove the excessive Thiourea solution, the surface of the electrode is rinsed with ethanol and Millipore deionized water and then dried using Nitrogen gas. The electrical insulation of the SAM layer is confirmed by evaluating the short circuit/current leakage using the 2 point probe station. Glutaraldehyde ($C_5H_8O_2$) was used to promote surface activation on the SAM layer, for enhanced antibody binding as shown in FIG. 4. The CA-125 antibodies of 10 ng/ml are placed on top of the Surface-activated SAM layer at 4° C. for 12 hours to immobilize the antibodies. A 10 mM of 1-dodecanthiol in ethanolic solution was added on top of the electrodes to block the unwanted sites or the bare spots on electrode surface (Limbut et al 2006).

The PDMS microchannel was bonded with the Si-wafer on with the nano interdigitated circuit fabricated, in order to have the biofluid sample flow on top of the immobilized CA-125 antibodies. The biofluid sample used in this example was with the concentration of 55 µg/ml of CA-125 antigens at pH 7.4.

FIG. 4 shows the schematic model of the various steps involved in surface activation and immobilization of the CA-125 antibodies on the gold electrodes.

The principles of the controlled self-driven flow of the biofluid in the PDMS microchannel using the surface treatment are discussed below. Again, this example utilizes blood as a biofluid, however the invention is in no way limited to utilizing blood as a biofluid sample as previously explained.

Figure 5:
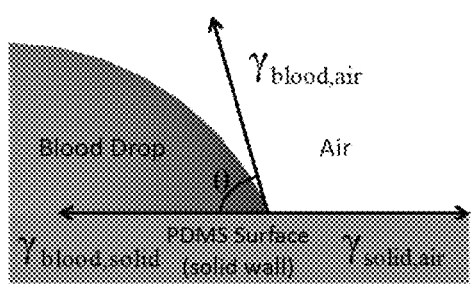
FIG. 5 illustrates a schematic of a blood drop on a PDMS surface with showing interfacial tensions and contact angle.

The contact angle of a liquid drop on a solid surface was defined in this example by the mechanical equilibrium of the drop under the action of the interfacial tensions. The three interfacial tensions observed when a blood drop is placed on a solid (PDMS) surface were $\gamma_{blood,air}$, $\gamma_{blood,solid}$ & $\gamma_{solid,air}$ where $\gamma_{blood,air}$ is the interfacial tension between blood and air, $\gamma_{blood,solid}$ is the interfacial tension between blood and PDMS substrate and $\gamma_{solid,air}$ is the interfacial tension between the PDMS substrate and air as shown in FIG. 5.

As per Young's law, $$\gamma_{solid,air} = \gamma_{blood,solid} + \gamma_{blood,air} \cos\theta \qquad \text{(Equation 1)}$$

From equation 1, the contact angle $\theta$ can be calculated using equation 2:

$$\theta = \cos^{-1}\left(\frac{\gamma_{solid,air} - \gamma_{blood,solid}}{\gamma_{blood,air}}\right) \qquad \text{(Equation 2)}$$

The surface tension driven flow can be controlled by altering the contact angle of the fluid with the surface. The contact angle of the fluid can be changed by various surface treatments to the surface on which the fluid is intended to flow. The contact angles of blood in this example or experiment was measured with a precision of an experimental uncertainty of ±2° of variation within the theoretical values. Capillary diameter of blood is determined by the Equation 3 as shown below:

$$\lambda_{blood} = \sqrt{\frac{\gamma_{blood}}{\rho_{blood} g}} \qquad \text{(Equation 3)}$$

According to Hrncir and Rosina (1996) the surface tension of the blood ($\gamma_{blood}$) at 22° C. is 55.89×10$^{-3}$ N/m and the density of the blood ($\rho_{blood}$) is 1060 kg/m3. Considering the acceleration due to gravity (g) as 9.81 m²/s, the capillary length of blood ($\lambda_{blood}$) is calculated as 2.31 mm as per Eq-3. Assuming the drop shape as sphere the blood drop radius is confined to 1 mm, since the diameter of the blood drop sample should be less than the capillary diameter of blood (2.31 mm). The volume of the blood drop used in the experiment with 1 mm radius is 4.2 µl. The assumptions made while measuring the contact angle are: [a] The roughness factor of PDMS is ignored, so that the contact angle variations were made just by the surface properties instead of the roughness effect. [b] The values of $\gamma_{blood,air}$, $\gamma_{blood,solid}$ & $\gamma_{soild,air}$ are assumed to be constant throughout the experiment. [c] The surface tension of the blood is higher than the surface tension of the PDMS with surface treatments. [d] The PDMS sample fabricated are rigid, smooth and homogenous.

The contact angle was varied with the duration of the plasma treatments to the PDMS. The contact angle of blood drop with the PDMS sample has decreased from 107.12° to 47.07° as shown in FIGS. 6A-6D and FIG. 7 with the plasma treatment duration from 0 sec to 100 sec.

FIGS. 6A-6D show the images of the drop placed on the PDMS that are treated with plasma for the duration of 0 sec, 25 sec, 75 sec and 100 sec. The contact angles measured for the drop on the PDMS surface that are treated with plasma for the duration of 0 sec, 25 sec, 75 sec and 100 sec are 107.12°, 88.12°, 62.65° and 47.07° respectively. FIG. 7 shows the plot of the contact angle variation with the duration of the plasma treatment. Increase in the duration of oxygen plasma treatment of PDMS samples decreased the contact angle made by the drop with the PDMS surface. This implies that the PDMS surface is converted from hydrophobic to hydrophilic with the oxygen plasma treatment.

Figure 8:
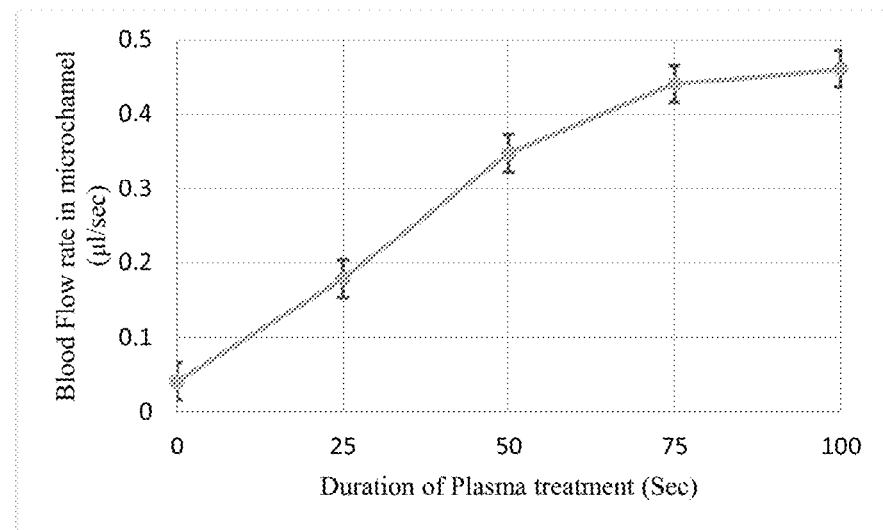
FIG. 8 illustrates Plot of flow rate of blood in microchannels on PDMS surfaces treated with oxygen plasma for various durations (0 sec, 25 sec, 75 sec, & 100 sec)

The blood flow in microchannel is self-driven due to the capillary effect induced by the surface tension of the blood. As the channel surfaces are plasma treated, the contact angle is controlled with the duration of plasma treatment. Since the contact angle controls the capillary effect induced in the blood volume, the duration of plasma treatment also control the blood flow in the microchannel. The plot of the blood flow rate in the plasma treated surfaces for various durations is shown in FIG. 8.

The blood flow rate in the microchannel has increased from 0.04 µl/sec to 0.46 µl/sec when the surface of the PDMS is treated with plasma from 0 sec to 100 sec. From FIG. 8, it was evident that the biofluid can be self-driven in microchannel with controlled flow rate by treating the surface of microchannel with various durations of the plasma treatment. The scope of this experiment was limited to demonstrate the self-driven flow of blood in microchannel with controlled flow rate.

The sensing mechanism implemented in the biochip used a non-optical methodology which can drastically reduce the setup cost and enhance the accuracy of the results. The biological formations and changes in the microchannel are captured using the nano interdigitated electrode circuit.

When the biofluid sample with antigens flow in the microchannel, over the antibodies that are immobilized on the nano circuit, the antigens from the sample interact with the antibodies and form the antigen/antibody conjugation. The antigen/antibody conjugation results in the change in the dielectric properties of medium and causes the change in the capacitance in the nano circuit. The antigens in the biofluid sample can be detected with the change in the capacitance measurement of the nano circuit.

As the antigen/antibody complex is unique, only specific antigen will from antigen/antibody conjugation with the specific antibody. By sensing the electrical signal (capacitance variation) from the antigen/antibody conjugation, the antigens in the biofluid sample can be detected.

Figure 9:
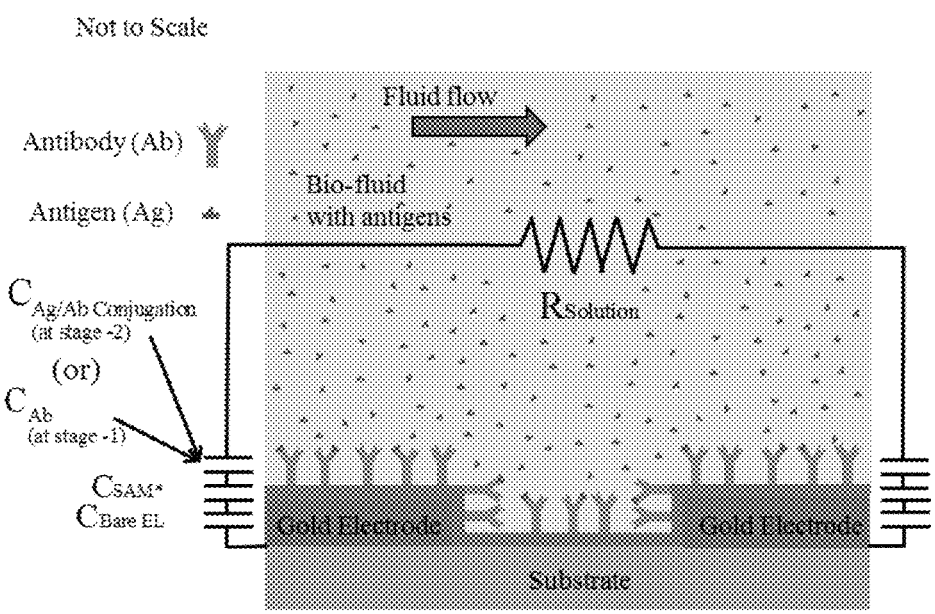
FIG. 9 illustrates a schematic representation of capacitance sensor circuit.

FIG. 9 explains the simplified schematic of the capacitance model of the sensing mechanism in the biochip. The layers which influence the capacitance in the comprised capacitance model are Bare electrodes ($C_{Bare\ EL}$), Surface-activated SAM layer ($C_{SAM*}$), Antibody ($C_{Ab}$) and Antigen/Antibody conjugation $$\left(\begin{matrix}C_{Ag/Ab}\\ \text{Conjugation}\end{matrix}\right).$$

At stage-1, the capacitance is measured before the antigen/antibody conjugation. At stage-2, the capacitance is measure after the antigen/antibody conjugation. The capacitance measured before the antigen/antibody conjugation is the 'Baseline' capacitance $$\left(\begin{matrix}C_{Baseline}\\ \text{(Before Ag/Ab conjugation)}\end{matrix}\right).$$

In 'Baseline' capacitance measurement, the Bare electrodes, Surface-activated SAM layer and Antibody layers are considered. The capacitance measured after the antigen/antibody conjugation is the 'Total' capacitance ( $$\left(\begin{matrix}C_{Total}\\ \text{(After Ag/Ab conjugation)}\end{matrix}\right).$$

In 'Total' capacitance measurement, the Bare electrodes, Surface-activated SAM layer and Antigen/Antibody conjugation layers are considered. The generic capacitance is calculated using the model as shown in FIG. 9.

Figures 10A, 10B:
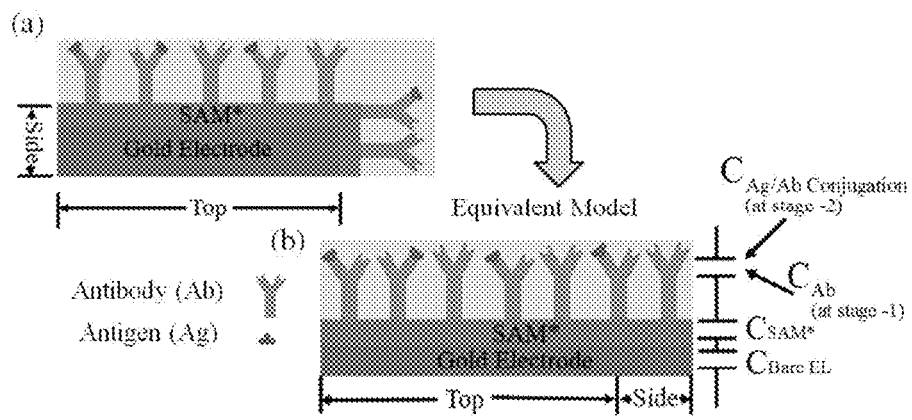
FIGS. 10A and 10B illustrate schematics.

The effective surface area of the electrode that contributes to the capacitance are, 'Top' surface area and 'Side' surface area as shown in FIG. 10A. The net capacitance 'C' of the active surface area (Top+Side) of the electrodes in the comprised capacitance model is given by the Equation 4, $$C = \varepsilon_r \cdot \varepsilon_0 \cdot \left(\frac{A_{\mathit{eff}_{Top}}}{d_{\mathit{eff}_{Top}}}\right) + \varepsilon_r \cdot \varepsilon_0 \cdot \left(\frac{A_{\mathit{eff}_{Side}}}{d_{\mathit{eff}_{Side}}}\right) \quad \text{(Equation 4)}$$

where $\varepsilon_r$ is the relative permittivity of the material between the electrodes and $\varepsilon_o$ is the vacuum permittivity, $A_{\mathit{eff}_{Top}}$ & $A_{\mathit{eff}_{Side}}$ are the effective surface areas on the Top and Side surfaces of the electrode, and $d_{\mathit{eff}_{Top}}$ & $d_{\mathit{eff}_{Side}}$ are the effective distances between the Top and Side surfaces of the electrodes.

When the SAM*, Antibody & Antigen/Antibody layers are assumed to be homogenous over the surface of electrode, the capacitance of the circuit can be calculated from the equivalent model, with the single surface (Top+Side) as shown in FIGS. 10A-10B.

Hence, the net capacitance 'C' of the circuit can be calculated as per Equation 5, $$C = \varepsilon_r \cdot \varepsilon o \cdot \left(\frac{A_{eff}}{d_{eff}}\right) \quad \text{(Equation 5)}$$

where $\varepsilon_r$ is the relative permittivity of the material between the electrodes and $\varepsilon_o$ is the vacuum permittivity, $A_{eff}$ is the effective surface area and $d_{eff}$ is the effective distance between electrodes. The capacitance of the Bare electrodes ($C_{Bare\ EL}$) in the nano circuit are calculated as per Equation 6, $$C_{Bare\ EL} = \varepsilon_{r_{Bare\ EL}} \cdot \varepsilon o \cdot \left(\frac{A_{eff_{Bare\ EL}}}{d_{eff_{Bare\ EL}}}\right) \quad \text{(Equation 6)}$$

where $\varepsilon_{r_{Bare\ EL}}$ is the relative permittivity of the material between the bare electrodes and $\varepsilon_o$ is the vacuum permittivity, $A_{eff_{Bare\ EL}}$ is the effective surface area of bare electrode, and $d_{eff_{Bare\ EL}}$ is the effective distance between the bare electrodes. Similarly the capacitances of the individual layers ($C_{SAM*}$, $C_{Ab}$ & $C_{Ag/Ab\ Conjugation}$) can be calculated using the Equation 5, with the corresponding $\varepsilon_r$, $\varepsilon_o$, $A_{eff}$, $d_{eff}$ values of each layer. It can be inferred from this equation, that a significant change in the capacitance can be caused in three ways: (i) by altering the distance $d_{eff}$ between the two electrodes, (ii) by altering the overlapping area $A_{eff}$ between the two electrodes and (iii) by a change in the dielectric permittivity between the electrodes. For the simplified case, assuming the interdigitated electrodes are sufficiently thick, the resistance 'R' in the solution is given by the Equation 7, $$R_{Solution} = \frac{1}{n \cdot l} \frac{1}{k} \frac{2 \cdot \sin\left(\frac{\pi \cdot d_{eff}}{2L}\right)}{\cos\left(\frac{\pi \cdot d_{eff}}{2L}\right)} \quad \text{(Equation 7)}$$

where n is the number of fingers and l is the length of fingers of the interdigitated electrodes, k is the conductivity of the biofluid sample, $d_{eff}$ is the spacing between the electrodes and L is the width of the electrode.

The capacitive measurements at different layer of the sensing platform were calculated using Agilent 4284A Electrical Analyzer. All the capacitive measurements were carried out in the frequency range of 10 Hz to 100 Hz with an increment of 10 Hz at a time. The variation in capacitance is due to the change in the dielectric properties of the double-layers from each interface that directly adds up to the capacitive series. The capacitance at the bare electrodes ($C_{Bare\ EL}$) is measured directly by connecting the probes of the electrical analyzer, to the contact pads of the Gold nano interdigitated electrodes. The capacitance measurements are from the bare electrodes without any layers on the electrodes. The capacitance of bare electrode is 9.4 nF at 10 kHz and then gradually decreased to 8.7 nF at 100 kHZ as shown in the FIG. 11.

Figure 11:
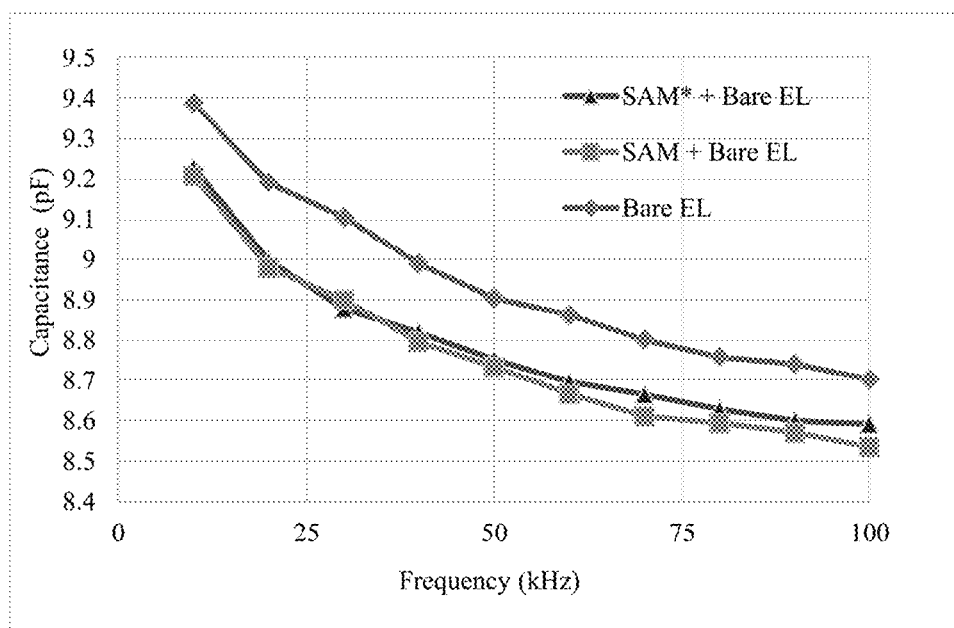
FIG. 11 illustrates a plot of capacitance measurements at bare electrodes, SAM layer, and Surface-activated SAM layer with frequency.

The SAM layer (Self-assembled monolayer) formed using the Thiourea ($CH_4N_2S$) on the gold interdigitated electrodes as shown in FIG. 3B. In Equation 8, $C_{SAM+Bare\ EL}$ is the capacitance at the SAM layer on the electrode. The capacitance at the SAM layer on the Bare electrodes ($C_{SAM+Bare\ EL}$) is measured by connecting the probes of electrical analyzer, to the contact pads of the gold nano interdigitated electrodes after the formation of SAM layer on the Bare electrodes. The capacitance measured at the SAM layer is 9.2 pF at 10 kHz and then dropped to 8.6 pF at 100 kHz. as shown in FIG. 11.

$$C_{SAM+Bare\ EL} = \left[\frac{1}{C_{SAM}} + \frac{1}{C_{Bare\ EL}}\right]^{-1} \quad \text{(Equation 8)}$$

where $C_{SAM}$ is the capacitance caused due to SAM layer and $C_{Bare\ EL}$ is the capacitance caused due to Bare electrodes.

The Glutaraldehyde ($C_5H_8O_2$) is used to activate the surface of the gold nano interdigitated electrodes with the self-assembled monolayer as shown in FIG. 4. The surface activation of the SAM layer is required to strengthen the bonding of the antibody (CA-125) to the monolayer. The Glutaraldehyde ($C_5H_8O_2$) replaces the Hydrogen ($H_2$) in Thiourea with one of the aldehyde group (—CHO) of Glutaraldehyde and form a bi-product ($H_2O$). Thus the Surface-activated SAM layer provide the feasibility for the amide group ($NH_2$) of CA-125 antibody, to replace the oxygen in the exposed aldehyde group of surface-activated SAM layer and form a bi-product ($H_2O$). Thus, the Glutaraldehyde helps in forming a strong linkage between the SAM layer (Thiourea) and the antibodies.

In Equation 9, $C_{SAM*}$, is the capacitance caused due to the Surface-activated SAM layer. The capacitance at the Surface-activated SAM layer on the Bare electrodes ($C_{SAM*+Bare\ EL}$) is measured by connecting the probes of electrical analyzer, to the contact pads of the gold nano interdigitated electrodes, after the surface activation of the SAM layer on the Bare electrodes. The capacitance measured at the Surface-activated SAM layer is 9.2 pF at 10 kHz and then reduced to 8.55 pF at 100 kHz as shown in FIG. 11.

$$C_{SAM*+Bare\ EL} = \left[\frac{1}{C_{SAM*}} + \frac{1}{C_{Bare\ EL}}\right]^{-1} \quad \text{(Equation 9)}$$

Figure 12:
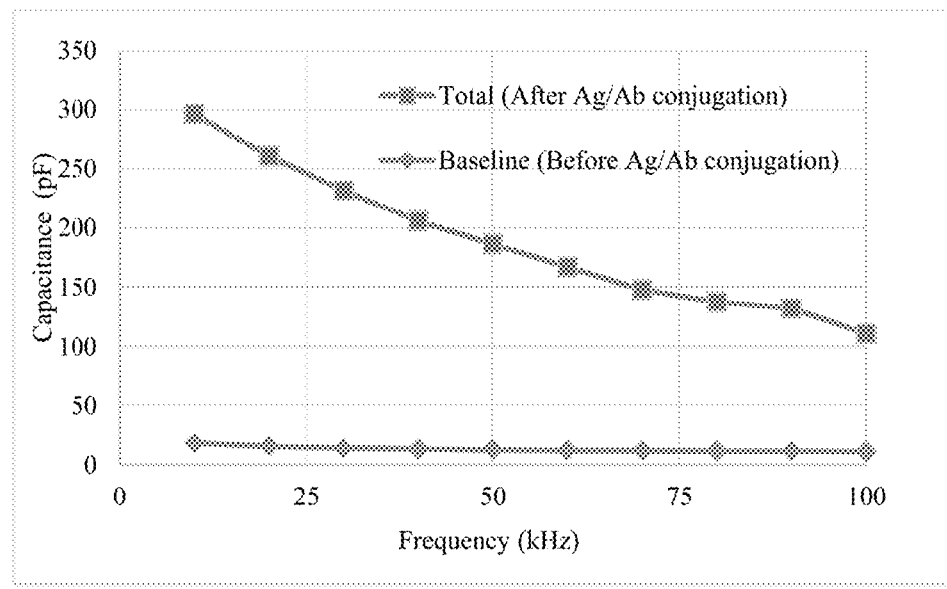
FIG. 12 illustrates a plot of capacitance measurements of total (after Ag/Ab conjugation) and baseline (before Ag/Ab conjugation) and with frequency.

Based on the capacitance measurements at Bare electrodes, SAM layer, and Surface-activated SAM layer at different frequencies, the following conclusions are made: (1) The significant difference of the capacitance measurements at the Bare electrodes ($C_{Bare\ EL}$) to the capacitance measurements at the SAM layer ($C_{SAM+Bare\ EL}$) and Surface-activated SAM layer ($C_{SAM*+Bare\ EL}$) is due to the adsorption of the thiol monolayer to the gold electrode surface which causes the significant change in the dielectric properties. (2) The difference in the capacitance measurements at SAM layer ($C_{SAM+Bare\ EL}$) and Surface-activated SAM layer ($C_{SAM*+Bare\ EL}$) is very minimal over the frequency, as the change in the dielectric properties at SAM layer and Surface-activated SAM layer is very minimal. Since, $C_{SAM+Bare\ EL} \approx C_{SAM*+Bare\ EL}$, it can be inferred that $C_{SAM} \approx C_{SAM*}$ In Equation 10 at stage-1, the capacitance at the Baseline $$\left(C_{Baseline} \atop {(Before\ Ag/Ab\ conjugation)}\right)$$

is measured after the CA-125 antibodies are immobilized on the surface-activated SAM later of the Gold nano interdigitated electrodes and before the antigen/antibody conjugation. The capacitance at the Baseline (before antigen/antibody conjugation) is measured by connecting the probes of electrical analyzer, to the contact pads of the gold nano interdigitated electrodes, after the immobilization of the CA-125 antibodies. The capacitance measurement at the immobilized antibody layer, before the antigen/antibody conjugation is 18.7 pF at 10 kHz and the reduced to 11.3 pF at 100 kHz as shown in FIG. 12.

$$C_{Baseline \atop (Before\ Ag/Ab\ conjugation)} = \left[\frac{1}{C_{Bare\ EL}} + \frac{1}{C_{SAM*}} + \frac{1}{C_{Ab}}\right]^{-1} \quad \text{(Equation 10)}$$

where $C_{Bare\ EL}$, $C_{SAM*}$ and $C_{Ab}$ are the capacitance due to Bare electrodes, Surface-activated SAM layer and Antibodies layer.

In Equation 11 at stage-2, the capacitance at the Total $$\left(C_{Total \atop (After\ Ag/Ab\ conjugation)}\right)$$

is measured After the CA-125 antigen/antibody conjugation, when the biofluid sample (with CA-125 antigens) flow in the microchannel under the controlled self-driven flow condition, over the immobilized CA-125 antibodies on the surface-activated SAM layer of the Gold nano interdigitated electrodes.

$$C_{Total \atop (After\ Ag/Ab\ conjugation)} = \left[\frac{1}{C_{Bare\ EL}} + \frac{1}{C_{SAM*}} + \frac{1}{C_{Ag/Ab\ Conjugation}}\right]^{-1} \quad \text{(Equation 11)}$$

where $C_{Bare\ EL}$, $C_{SAM*}$ and $C_{Ag/Ab\ Conjugation}$ are the capacitance due to Bare electrodes, Surface-activated SAM layer and Antigen/Antibody Conjugation layer. The change in the net molecular size due to antigen/antibody conjugation creates a disturbance in the distribution of charges, and creates a dipole moment at the dielectric interface. The hydrocarbon chains present in the proteins are polar in nature. The net charge variation due to the interaction of the hydrocarbons of antibodies and antigens creates a process of local polarization that directly influences the dielectric permittivity of the antigen/antibody conjugation on the electrode surface. The dipole-dipole interaction stimulates the polarization on the electrode surface. With this phenomenon, the dielectric of each antigen/antibody conjugation has unique characteristic over the range of frequencies, which helps to identify the conjugation formation. The 'Total' capacitance after CA-125 antigen/antibody conjugation is 296 pF at 10 kHz, which reduced to 110.9 pF at 100 kHz as shown in FIG. 12. As per Equation 12, the difference in capacitance (ΔC) between stage-1 and stage-2 (from Equations 10, 11 & 12), provides the information of capacitance change caused due to the conjugation of antigen/antibody, which indicate the existence of antigens in the biofluid sample.

$$\Delta C = C_{Total \atop (After\ Ag/Ab\ conjugation)} - C_{Baseline \atop (Before\ Ag/Ab\ conjugation)} \quad \text{(Equation 12)}$$

Based on the capacitance measurements at the Baseline (Before Ag/Ab conjugation) and at 'Total' (After Ag/Ab conjugation) during the biofluid sample flow on the sensing mechanism, at different frequencies, the following conclusions are made: (1) The capacitance measurements of Total (After Ag/Ab conjugation) are decreasing from 296 pF to 110.9 pF, with the increase in the frequency from 10 kHz to 100 kHz, because as the frequency increases, the net polarization in all the layers on the interdigitated electrode decreases, that directly influence the dielectric properties. The decrement in the dielectric value reduces the capacitance with the increment of frequency. With the same reason, the capacitance measurements of Baseline (Before Ag/Ab Coagulation) are also decreasing from 18.7 pF to 11.3 pF, with the increase in the frequency from 10 kHz to 100 kHz, but the change in capacitance is not evident in the plot FIG. 12, due to the scale of the plot. (2) The capacitance measurements at Total (After Ag/Ab conjugation) is higher than the Baseline (Before Ag/Ab conjugation) over the frequency because as the dielectric permittivity of the CA-125 antigen/antibody conjugation is directly increased by local polarization, which is due to the net charge variation with the interaction of the hydrocarbons of antigens and antibodies.

From the observations it is understood that the functionality of the sensing mechanism is successfully evaluated under the controlled self-driven flow condition with the significant change of capacitance values from 'Baseline' to 'Total'.

Figure 13:
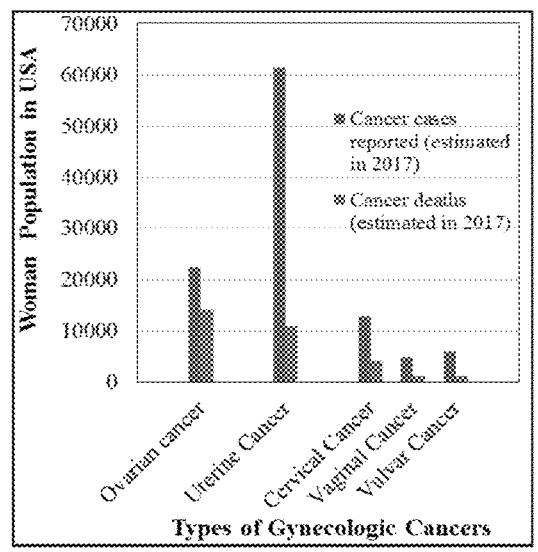
FIG. 13 illustrates a plot of gynecologic diseases effecting woman population (USA) in 2017.

The American Cancer Society stated that a total of 1,688,780 new cancer cases and 600,920 deaths from cancer are projected to occur in the United States of America in 2017 (as per the Cancer Facts and Figures, 2017). Cancer still remains the second most common cause for death in the United States, which is about 1 in every 4 deaths. Ovarian cancer ranks as the fifth most common cancer in women Though there are high number of cases being reported for Uterine Cancer among all the gynecological cancers, Ovarian cancer has the highest mortality rate among all the gynecologic malignancies (as shown in FIG. 13).

In 2017, there is an estimated 22,440 new ovarian cancer cases to be reported and 14,080 ovarian cancer deaths are expected to occur (in USA). Ovarian cancer deaths are 5% among all the cancer deaths of woman.

Figure 14:
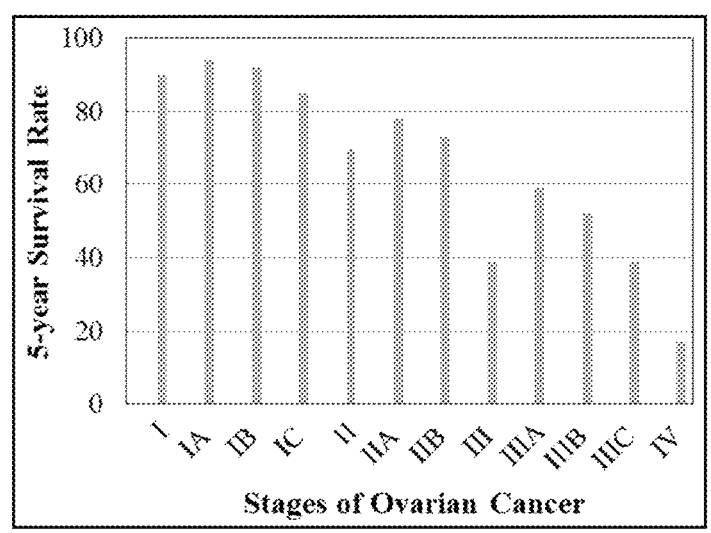
FIG. 14 illustrates a plot of 5-year survival rate of the ovarian disease patients at each stage.

The current available technologies can only detect only 15% of ovarian cancer cases at early stages (ie., stage 1A & stage 1B), with the survival rate of 93%, while the remaining 85% of ovarian cancer cases are detected at the advanced stages, with the survival rate being just 31% (as shown in FIG. 14). The significant rise of the survival rate of these cancer cases emphasizes the need of early stage diagnosis.

Enabling the cancer diagnosis as an easy and simple process can increase the number of diagnosis and thus have an increased chance of early stage diagnosis. National Cancer Institute (NCI) stated that there has been no effective screening tests exists for early detection of many cancers. Cancer diagnostics is still a frontier that has not been completely explored by biochip researchers.

In this second example, the POC micro biochip is primarily intended to diagnose the ovarian cancer at the early stage with a blood sample from a finger prick. The POC micro biochip is an immune-assay which can detect the cancer antigens in the blood at very low concentration. The change in the capacitance measurement of the nano circuit of the biochip indicated the formation of antigen/antibody complex.

Early Stage Ovarian Cancer Biomarkers

The best technologies currently available for early detection of the ovarian cancers are the combination of screenings of elevated CA-125 and transvaginal ultrasound—TVS (when elevated levels of CA-125 are detected). However these technologies do not meet the criteria for cost effectiveness espoused by United States Preventive Services Task Force. Therefore there has been no screening recommended by any professional group for ovarian cancer in general public. FIG. 15 illustrates a table of specificity and sensitivity of early detection ovarian cancer biomarkers from various studies.

The elevated levels of CA-125 are not present in the 20% of the ovarian cancer patients and also the elevated levels of CA-125 are shown in benign conditions such as liver cirrhosis, endometriosis and peritonitis. CA-125 levels also fluctuate with due to pregnancy and menstrual cycles. However CA-125 has been effectively used in conjugation with other biomarkers such as Human Epididymis Protein 4 (HE-4), Alpha-fetoprotein Receptor (RECAF), Prostasin, Apolipoprotein A-1 (Apo-A1) and Transthyretin (TTR) to increase its sensitivity and specificity as the early detection biomarkers (as shown in FIG. 15).

The threshold value is the concentration of biomarker in serum that indicates the existence of ovarian cancer. It is the concentration of the biomarker that differentiates the ovarian cancer patients (OVC) from the normal population. The limit of detection is acquired by the standard assays. The concentration of biomarker HE-4 naturally increases with age. Older women will have higher concentration of HE-4 that younger woman. Apo-A1 and TTR, when used with CA-125 yield highest sensitivity and specificity. However, Apo-A1 and TTR are under expressed in OVC patients. OVC patients will have lower concentration of Apo-A1 and TTR compared to healthy people. The POC biochip uses the conjugation of biomarkers that are listed above in order to detect the ovarian cancer at the early stages.

Point-of-Care (POC) Micro Biochip Design

Figure 16:
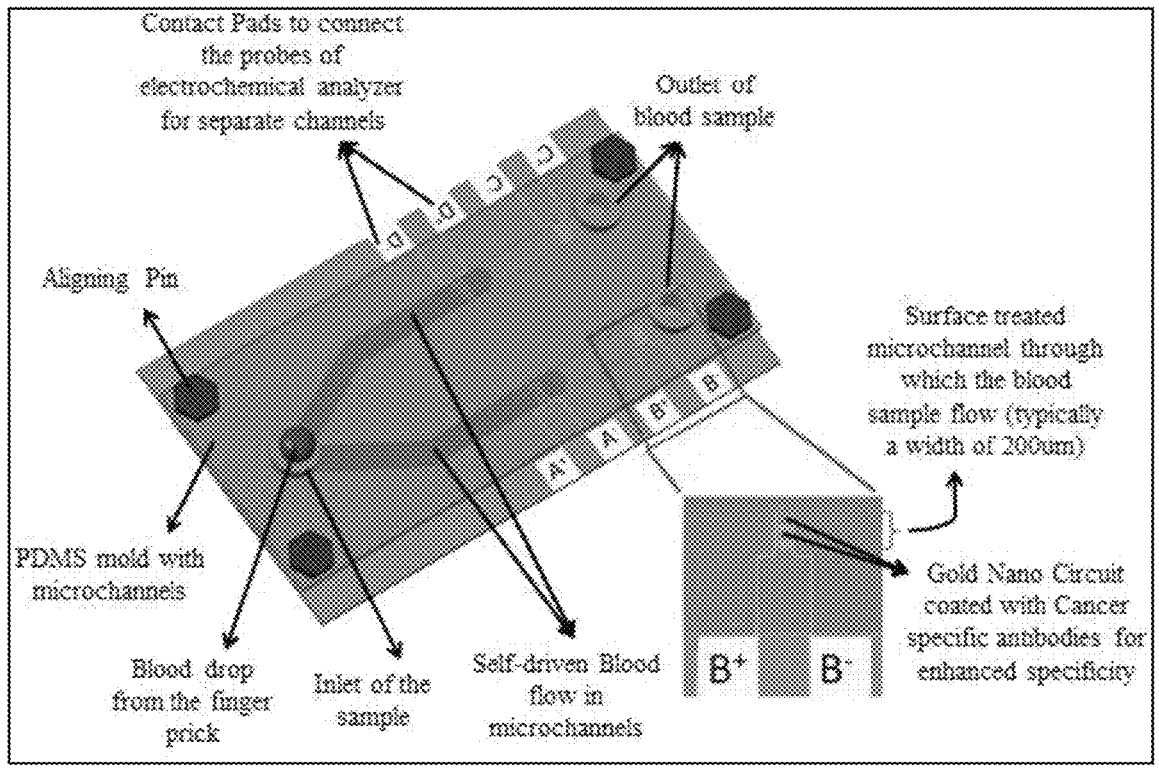
FIG. 16 illustrates a schematic model of a POC micro biochip incorporated with microchannels and nano circuit.

The POC micro biochip is incorporated with surface treated microchannels to control the self-driven flow of blood sample without any external flow control devices and a capacitance sensing mechanism to detect the biological interactions such as antigen (Ag)-antibody (Ab) complex formation (as shown FIG. 16). The biochip is designed with multichannel distribution from a single inlet of the blood sample, to improve the feasibility of detecting multiple antigens using multiple antibodies coated in different channels. Detecting the multiple cancer antigens from the same sample can enhance the sensitivity of the biochip. In POC biochip the multiple gold nano Interdigitated Electrodes (IDE) are incorporated at different sections of the microchannel to sense the biological interactions with the enhanced signal and thus also increase the sensitivity. The gold nano IDEs are connected to individual contact pads, to monitor the signal from each IDE separately. Attaching each IDE with a unique cancer antibody helps to sense the signal of the corresponding antigen/antibody complex formation individually and thus the individual concentrations of the specific antigens in the blood sample can be detected. The existence of ovarian cancer can be determined from the blood sample, by detecting the corresponding ovarian cancer antigens. Thus the POC biochip can detect ovarian cancer existence and its severity, by detecting the cancer antigens existence and its composition in the blood sample.

Surface Treated Microchannels

Figure 17:
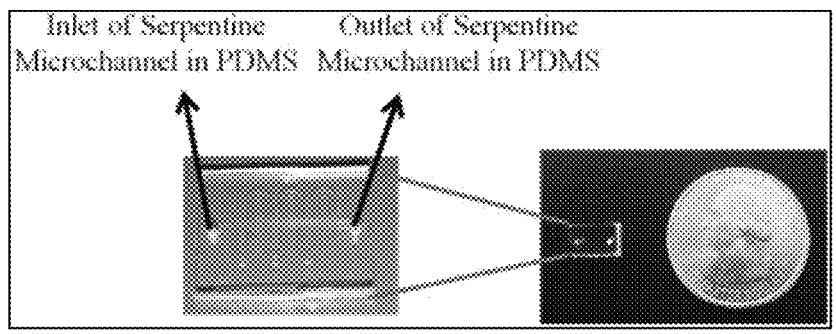
FIG. 17 illustrates a PDMS mold with serpentine microchannel of 200 um width and 107 um height with U.S. quarter coin for representative size.

The microchannels are designed with the specific aspect ratios (width of about from 200 μm to 500 μm and depth of about 107 μm) to amplify the self-driven capillary flow and self-separation of plasma from blood. A Si wafer of 4 inch diameter is cleaned and spin coated with a positive photoresist (SPRTM 955), which is then exposed to UV rays using the UV mask aligner for 14 seconds. The wafer is then treated with CD-26 and DI water to let the photoresist remain only at the microchannel structures. The Si wafer was then etched using Deep Reactive Ion Etching (DRIE) to 107 um, which elevate the microchannel structures and remove the material from rest of the areas. Polydimethylsiloxane (PDMS) was mixed with appropriate composition (1:10) and then poured on top of etched Si-wafer with microchannel structures after degassing at vacuum chamber. The PDMS along with the Si wafer was baked at 60 degree centigrade for an hour. Then the PDMS layer was carefully peeled and made holes for the inlet and outlet to the microchannel as shown in the FIG. 17. The PDMS mold was then aligned with Si-wafer with nano circuit.

PDMS is highly inert and hydrophobic in its nature. To convert the PDMS to hydrophilic, the PDMS surface is exposed to oxygen plasma for various durations. In this example, the hydrophilicity of PDMS was controlled by the variation in duration of the plasma treatment. The plasma treatments are performed on the 'Plasma Cleaner-PDC-32G' with oxygen flow rate of 20 sccm and 98.8 bar pressure. The radio frequency (RF power supply-150 W) of 13.56 MHz frequency was used for plasma excitation.

Gold Nano Interdigitated Circuit

Figure 18:
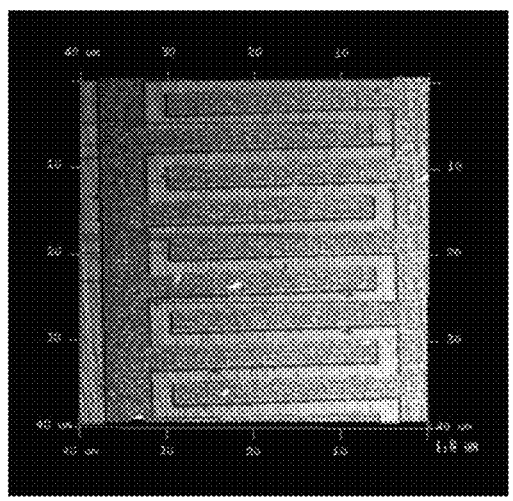
FIG. 18 illustrates an Atomic Force Microscopic (AFM) image of the gold interdigitated electrodes.

To fabricate the gold nano circuit on the Si wafer, it is initially cleaned with isopropanol and coated with a positive photoresist (PMMA-A6). Considering the required height of the PMMA, the spin coater is set to appropriate speed and later it is dried before it follows the lithography steps at the Electron Beam Lithography (EBL) tool. The desired nano circuit pattern is formed on the Si wafer after it is washed with MIBK:IPAf for 60 seconds. To improve the adhesion between gold and silicon, a layer of Titanium (app 10 nm) is deposited. 90 nm of gold is deposited on the nano circuit patterned Si wafer, using the Physical Vapor Deposition (PVD) process using Kurt J Lesker PVD-75 Evaporator. The lift-off process is implemented to remove the photoresist by cleaning with Acetone ultrasonic bath and later dried with nitrogen gas. Thus the gold nano interdigitated electrodes are formed as shown in FIG. 18.

Figure 19:
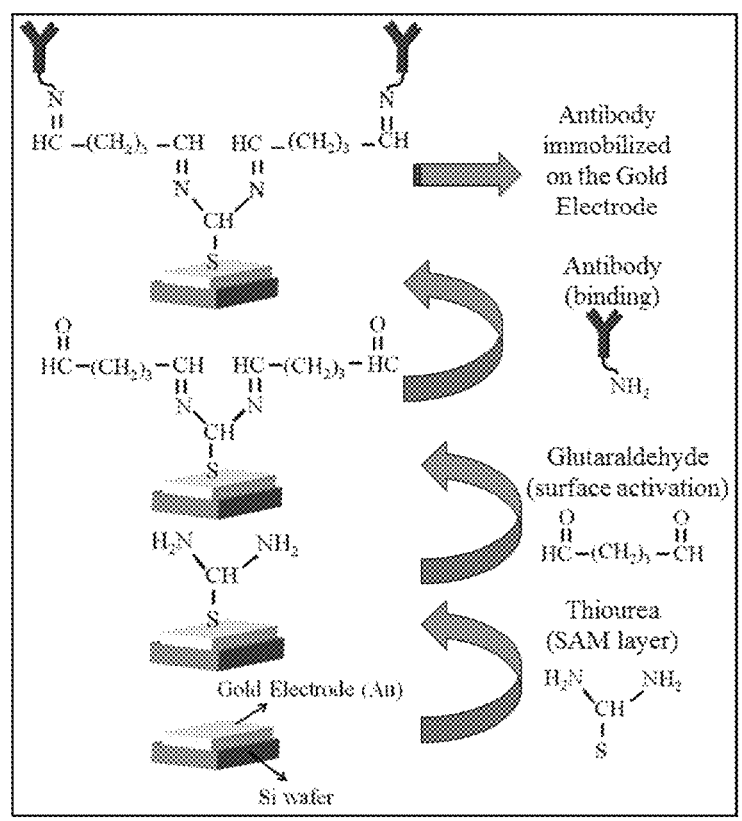
FIG. 19 illustrates a schematic representation of CA-125 Disease antibody immobilization on nano gold interdigitated electrodes.

The gold nano electrodes are insulated with the Self-assembled monolayer (SAM) and then coated with cancer antibodies. To form the SAM layer, the electrodes were immersed in a 50 mM Thiourea solution for 12 hours. Then the surface of the electrodes is rinsed with ethanol and Millipore deionized water and dried using Nitrogen gas. Glutaraldehyde was used to promote surface activation on the SAM layer. The ovarian cancer specific antibodies are aliquotted with a concentration of 10 ng/ml and then placed on top of the surface activated SAM layer at 4° C. for 12 hours to immobilize the antibodies. To block the unwanted sites or the bare spots on electrode surface a 10 mM of 1-dodecanthiol in ethanolic solution was added on top. Thus the cancer specific antibodies are immobilized on gold nano interdigitated electrodes as shown in FIG. 19.

The PDMS mold with microchannels is properly aligned with the nano patterned interdigitated circuit to facilitate the blood sample to flow on the cancer antibodies that are immobilized on the nano circuit in order to form antigen/antibody complex as shown in FIG. 16.

Results and Discussion

Controlled Self-Driven Flow of Blood in Microchannel

The contact angle of the blood drop on the solid (PDMS) surface is defined by the mechanical equilibrium of the drop, with the influence of the interfacial tensions. The three interfacial tensions identified when a blood drop is placed on a solid (PDMS) surface are $\gamma_{blood,air}$, $\gamma_{soild,air}$ & $\gamma_{blood,solid}$, where $\gamma_{soild,air}$ is the interfacial tension between the PDMS surface and air, $\gamma_{blood,air}$ is the interfacial tension between the blood and air and $\gamma_{blood,solid}$ is the interfacial tension between blood and PDMS surface as shown in FIG. 5.

Again, as per Young's law, $$\gamma_{solid,air} = \gamma_{blood,solid} + \gamma_{blood,air} \cos\theta \quad (1)$$

From eq (1), the contact angle θ can be calculated, as shown eq (2), $$\cos\theta = \left( \frac{\gamma_{solid,air} - \gamma_{blood,solid}}{\gamma_{blood,air}} \right) \quad (2)$$

Figure 20:
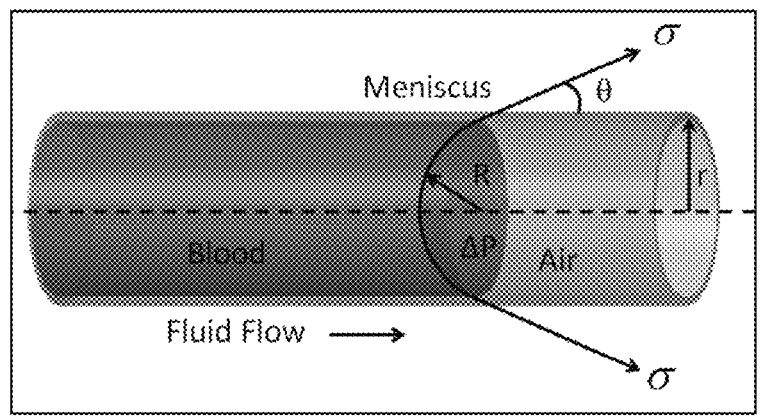
FIG. 20 illustrates a schematic of the biofluid flowing in capillary channel due to surface tension.

The surface tension is the primary cause of the capillary pressure difference across the interface between two fluids (liquid and air). The schematic of the microchannel (FIG. 20), of circular cross section with radius r, that is filled with two immiscible fluids (blood and air) with surface tension σ, the meniscus is approximated as a portion of a sphere with radius R, and the pressure difference across the meniscus is:

$$\Delta P = -\frac{2\sigma}{R} \quad (3)$$

The radius R of the meniscus depends only on the contact angle θ and the radius of the channel r as in eq-4:

$$\Delta P = -\frac{2\sigma \cos\theta}{R} \quad (4)$$

Figure 27:
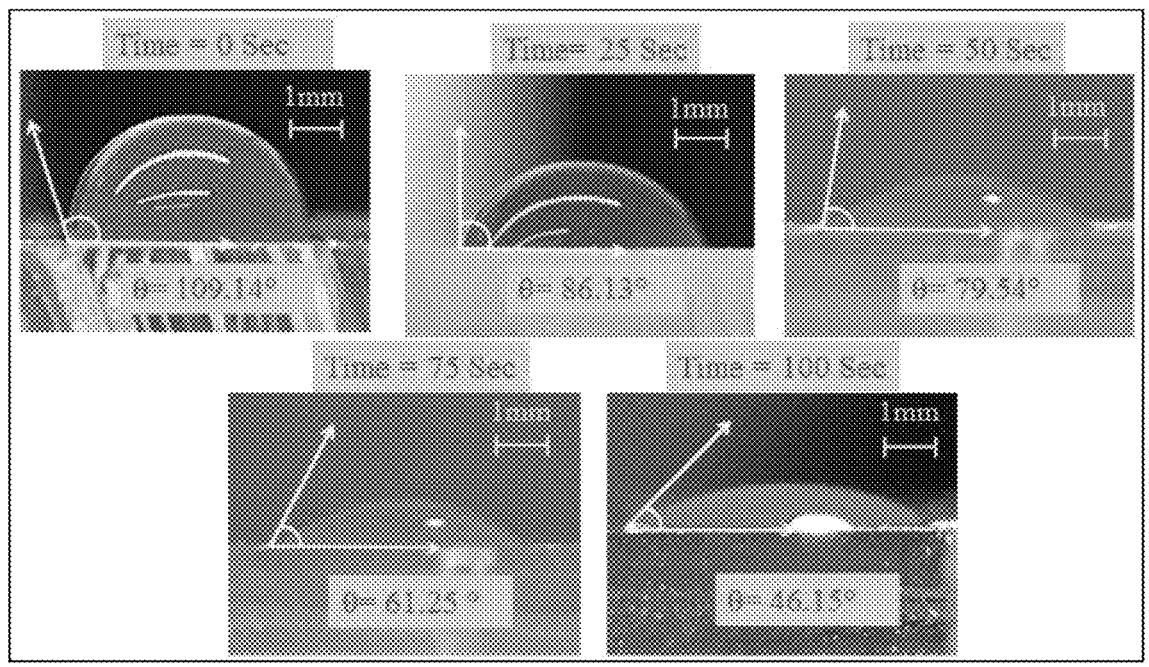
FIG. 27 illustrates Blood Drop Images (4.2 µl volume) on PDMS surface treated with oxygen plasma for various durations.

The contact angle of the blood drop is measured at the various durations of the plasma treatment to understand the hydrophilicity of the PDMS surface and to understand the flow rate of blood in microchannel. The contact angle measured with no plasma treatment to PDMS is 109.14°. The contact angles measured at 25 seconds, 50 seconds, 75 seconds and 100 seconds duration of the plasma treatment are 86.13°, 79.54°, 61.25° and 46.15° respectively (as shown in FIG. 27). FIG. 27 is Blood Drop Images (4.2 μl volume) on PDMS surface treated with oxygen plasma for various durations.

The surface treatment on the PDMS surface helps in controlling the contact angle from a range of 109.14° to 46.15° (FIG. 27). Increasing the duration of oxygen plasma treatment to PDMS surface has decreased the contact angle of the blood drop on the PDMS surface. This explains that the PDMS surface is converted from hydrophobic to hydrophilic nature with the duration of surface treatment.

Figure 28:
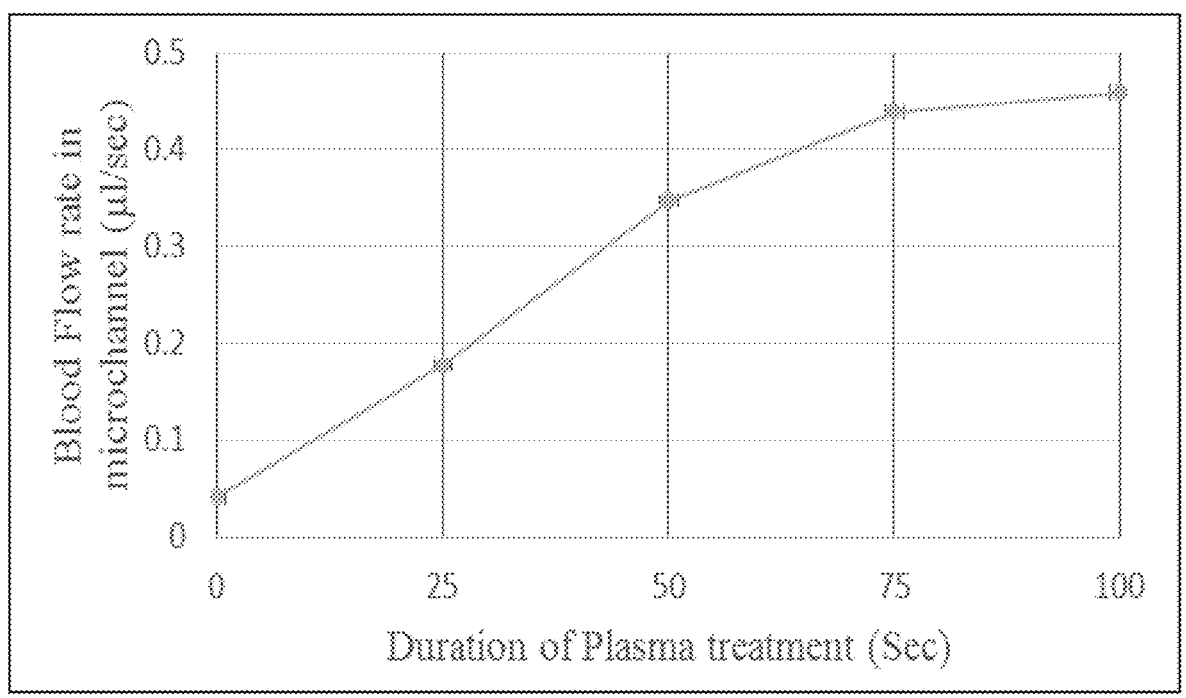
FIG. 28 illustrates a plot of the flow rate variation with the surface treatment duration.

By varying the contact angle of the fluid with the necessary surface treatments to the surface of microchannel helps in controlling the self-driven flow, when driven by the surface tension. The blood flow rate in microchannel has increased from 0.03 μl/sec to 0.47 μl/sec, when the surface of microchannel is treated from 0 seconds to 100 seconds as shown in FIG. 28. Therefore the flow rate of capillary driven blood flow in microchannel can be controlled by the duration of the plasma treatment in the microchannel.

Sensing Cancer Antigen from the Biofluid Sample

Figure 21:
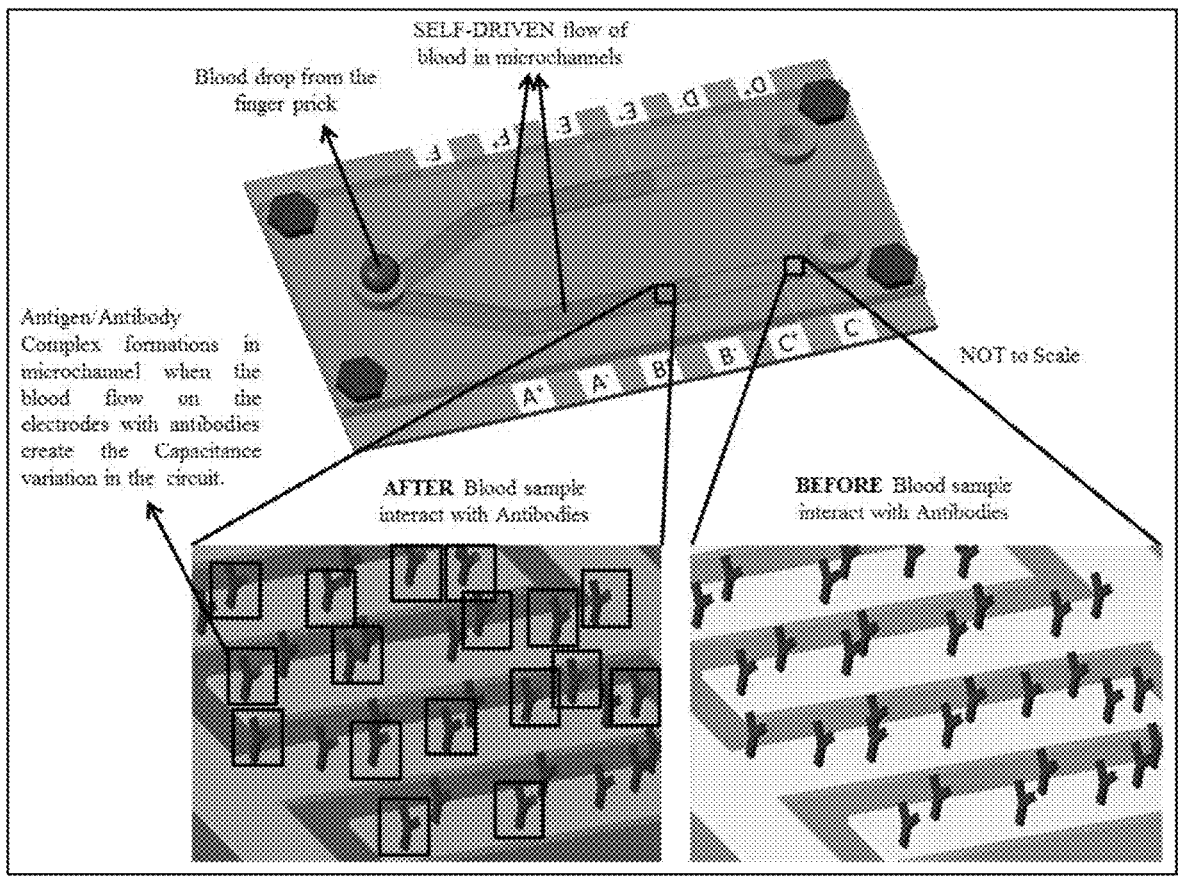
FIG. 21 illustrates a schematic of POC micro biochip functionality during the blood sample flow in microchannels.

In POC micro biochip, an electrical methodology (measuring change in capacitance) is implemented for the sensing antigen-antibody interaction as shown in FIG. 21. The electrical biosensor in the biochip detects the biomolecular reactions and interactions with the changes in electrical properties like voltage, current, impedance, capacitance, and the like. The approach of measuring the capacitance has advantages like high sensitivity, even for small changes (femto scale), freedom of sensor size variation and low power consumption requirement.

When the biofluid sample with ovarian cancer antigens flow in the microchannel, over the ovarian cancer antibodies that are immobilized on the nano circuit, the antigens from the sample interact with the corresponding antibodies and form the antigen/antibody complex. As the antigen/antibody complex is unique, only the ovarian cancer specific antigen will from antigen/antibody complex (Ag/Ab complex) with the ovarian cancer specific antibody. The antigen/antibody complex results in the change of the dielectric properties of medium and thus causes the change in the capacitance of the nano circuit. With the change in the capacitance measurement of the nano circuit the existence of the antigens in the biofluid sample can be detected as shown in FIG. 21.

Figure 22:
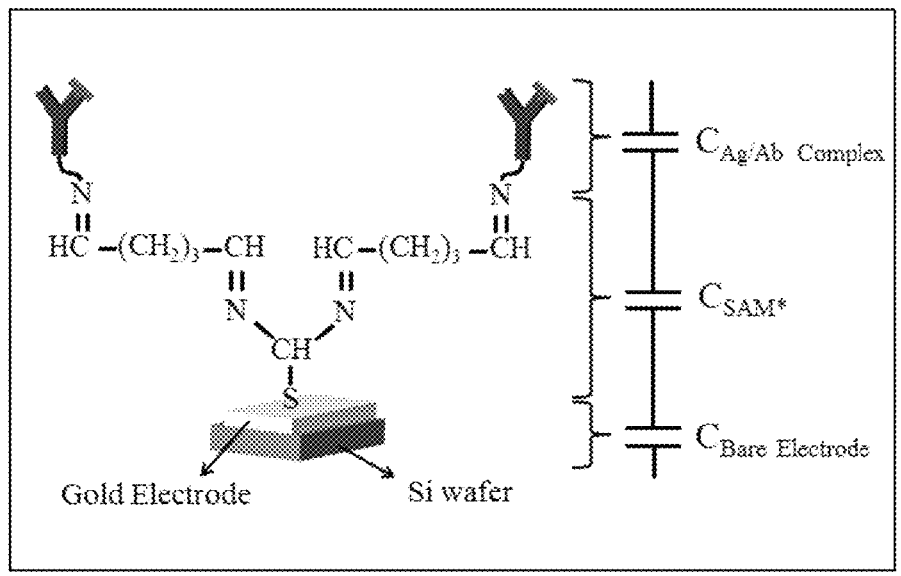
FIG. 22 illustrates a schematic model of capacitance nano interdigitated circuit.

FIG. 22 explains the simplified schematic of the capacitance model of the sensing mechanism in the biochip. The primary layers of sensing mechanism that influence the capacitance measurements are bare electrodes ($C_{Bare\ EL}$), surface-activated SAM layer ($C_{SAM*}$), ovarian cancer Antibody ($C_{Ab}$) and ovarian cancer Antigen/Antibody complex $$\left( \begin{array}{c} C_{Ag/Ab} \\ Complex \end{array} \right)$$

as shown in FIG. 22.

All the capacitive measurements were carried out in the frequency range of 10 Hz to 100 Hz with an increment of 10 Hz at a time using the Agilent 4284A Electrical Analyzer. The capacitance at the bare electrodes ($C_{Bare\ EL}$) is measured by connecting the probes of the electrical analyzer, to the contact pads of the gold nano interdigitated electrodes. Similarly the capacitance at different layers is measured by connecting the probes to the contact pads of the gold nano interdigitated electrodes with different layers on them.

At stage-1, the capacitance at the Baseline $$\left( \begin{array}{c} C_{Baseline} \\ (Before\ Ag/Ab\ complex) \end{array} \right)$$

is measured after the immobilization of the ovarian cancer specific antibodies (before the ovarian cancer antigen/antibody complex formation) as in eq-5.

$$C_{Baseline \atop (Before\ Ag/Ab\ complex)} = \left[ \frac{1}{C_{Bare\ El}} + \frac{1}{C_{SAM*}} + \frac{1}{C_{Ab}} \right]^{-1} \quad (5)$$

where $C_{Bare\ EL}$, $C_{SAM*}$ and $C_{Ab}$ are the capacitance due to bare electrodes, surface-activated SAM layer and antibodies layer.

At stage-2, the capacitance at the Total $$\begin{pmatrix} C_{Total} \\ (After\ Ag/Ab\ complex) \end{pmatrix}$$

is measured after the ovarian cancer antigen/antibody complex formation (as in eq-6), when the biofluid sample (with ovarian cancer antigens) flow in the microchannel under the controlled self-driven flow condition, over the immobilized ovarian cancer antibodies on the surface-activated SAM layer of the Gold nano interdigitated electrodes.

$$C_{Total\ (After\ Ag/Ab\ conjugation)} = \left[\frac{1}{C_{Bare\ EL}} + \frac{1}{C_{SAM*}} + \frac{1}{C_{Ag/Ab\ Conjugation}}\right]^{-1} \quad (6)$$

where $C_{Bare\ EL}$, $C_{SAM*}$ and $C_{Ag/Ab\ Conjugation}$ are the capacitance due to Bare electrodes, Surface-activated SAM layer and Antigen/Antibody Conjugation layer.

The 'Total' capacitance after ovarian cancer antigen/antibody complex formation is 270.09 pF at 10 kHz, which reduced to 95.92 pF at 100 kHz as shown in FIG. 13. As per eq-7, the change in capacitance ($\Delta C$) between the stage-1 & stage-2 (from eq-5 & 6), provides the information of the capacitance change due to formation of ovarian cancer antigen/antibody complex, which indicated the ovarian cancer antigens in the biofluid sample.

$$\Delta C = C_{Total\ (After\ Ag/Ab\ complex)} - C_{Baseline\ (Before\ Ag/Ab\ complex)} \quad (7)$$

Figure 23:
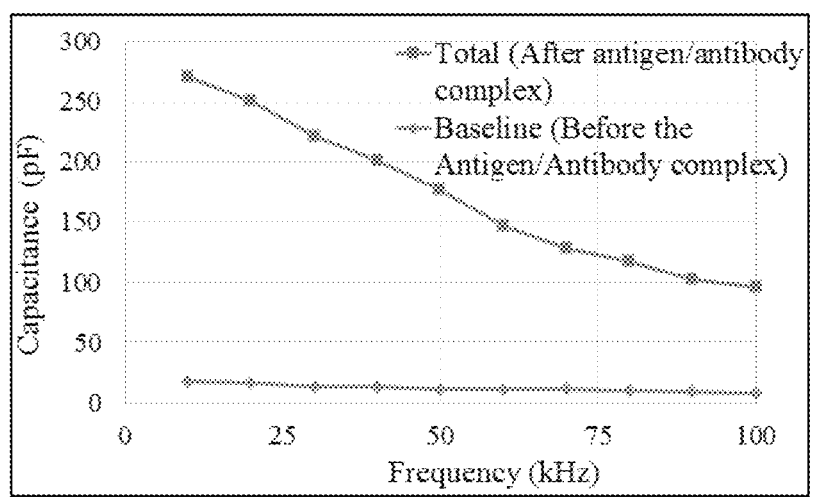
FIG. 23 illustrates a plot of capacitance measurements of total (after Ag/Ab complex) and baseline (before Ag/Ab complex) and with frequency.

The capacitance measurements of Total (After Ag/Ab complex) are decreasing from 270.09 pF to 95.92 pF, with the increase in the frequency from 10 kHz to 100 kHz, since as the frequency increases, the net polarization in all the layers on the interdigitated electrode will decrease, that directly influence the dielectric properties. The decrement in the dielectric value reduces the capacitance with the increment of the frequency values. With the same reason, the capacitance measurements of Baseline (Before Ag/Ab Complex) are also decreasing from 18.7 pF to 11.29 pF, with the increase in the frequency from 10 kHz to 100 kHz, but the change in capacitance is not properly evident in the plot (FIG. 23), due to the its scale.

In other embodiments, the principles of the invention may be incorporated into other physical manifestations. Below are a few examples and are not meant to limit the scope of the invention.

Figure 24A:
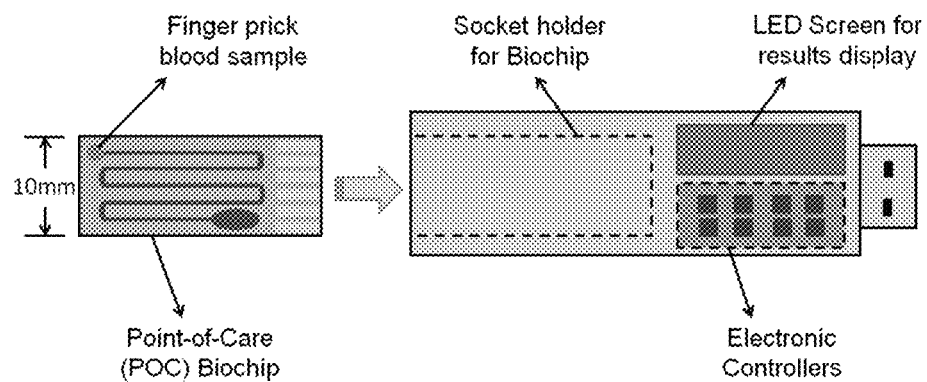
FIGS. 24A and 24B illustrate Point-of-Care (POC) Biochips.
Figure 24B:
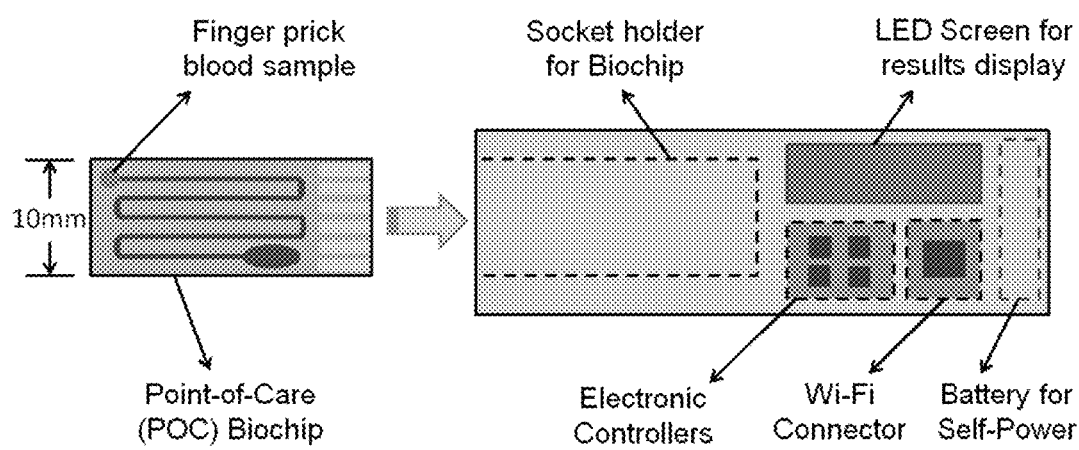

FIGS. 24A and 24B illustrates Point-of-Care (POC) Biochips, FIG. 24A illustrates a Point-of-Care (POC) Biochip as USB device and FIG. 24B illustrates a Point-of-Care (POC) Biochip as IOT device.

Figure 25:
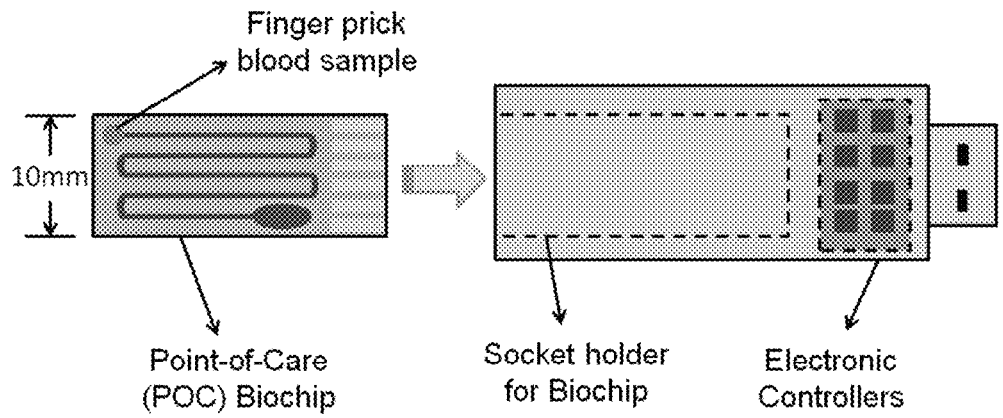
FIG. 25 illustrates a Point-of-Care (POC) Biochip as USB device supported with software to display the results on a laptop to which a USB is connected.

FIG. 25 illustrates a Point-of-Care (POC) Biochip as USB device supported with software to display the results on a laptop to which a USB is connected.

Figure 26:
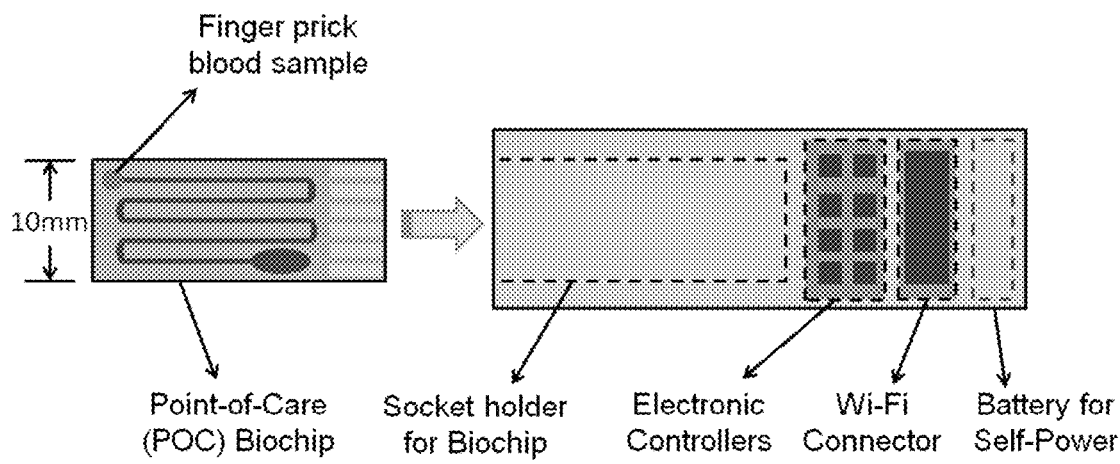
FIG. 26 illustrates a Point-of-Care (POC) Biochip as IOT device supported with software to display the results in a wireless device.

FIG. 26 illustrates a Point-of-Care (POC) Biochip as IOT device supported with software to display the results in a wireless device.

The self-driven flow in the microchannel is controlled by the surface treatments on the microchannel surface. The controlled flow rate in microchannels provides necessary conditions for biological reactions like antigen-antibody complex formation. Controlling the flow rate without any external devices helps to minimize the contamination of the sample. The change in the capacitance due to the ovarian cancer antigens in the blood sample helps to determine the existence of cancer. The biochip research is currently progressing to detect the early stage ovarian cancer antigens in pico and femto level concentrations with the enhanced sensing mechanism. The information of existence of early stage ovarian cancer antigens in the blood sample, enables the physicians to schedule the patient for next level of cancer diagnosis. This research work promotes in developing new standalone POC devices to detect the ovarian cancer at early stages and save thousands of woman.

Example II

The detection and determination of the cancer biomarkers are very crucial to diagnose at the early stages of the disease. The biosensor of the present disclosure improves the detection by reducing the process time, cost and space of the device. A surface modification protocol is utilized for better sensitivity under shear flow rate conditions using carbon nanotubes (CNTs). An interdigitated electrode transducer was modified using functionalized CNTs for signal enhancement. The biosensor was integrated with PDMS microfluidic channels for controlled self-driven flow. Experimental results shown indicate disease-specific antigens, such as CA-125, are detected using the principles of the present disclosure from a micro volume of biofluid sample using the CNTs modified interdigitated electrodes under capillary flow condition. This result is a vast improvement over current state of the art biosensors.

In general, the invention overcomes the disadvantages of past attempts to detect disease-specific antigens. Again as used herein, "sample" refers to a sample from a mammalian patient. Non-limiting examples of a sample include tissue or bodily fluids. Bodily fluids can include blood, urine, saliva, spinal fluid, any combination of these, or any other fluid originating in the body. Where blood is referenced specifically, it is referred to merely for illustrative purposes and is in no way meant to limit the scope of the invention. The following examples are given merely for illustrative purposes only and are in no way meant to limit the scope of the invention to these specific examples.

Materials and Methods
Chemicals and Apparatus

Phosphate buffer saline (PBS), 1-ethyl-3-(-3-dimethylaminopropyl) carbodiimide (EDC), N-hydroxysuccinimide (NHS), Carboxy functionalized Carbon nanotubes (CNTs), Thiourea ($CH_4N_2S$) were purchased from Sigma Aldrich (USA). The CA-125 monoclonal antibodies and the CA-125 antigens were purchased from Meridian Life Science. The Polydimethylsiloxane (PDMS) base and curing agent were bought from Fisher Scientific. De-ionized water was used throughout the experiments.

Sensor Fabrication

The Interdigitated nanoelectrodes are developed using photolithography technique. A thermal oxidized based silicon wafer is spin coated with a positive tone photoresist PMMA-6. The coated silicon wafer is patterned using JEOL JBX6300-FS Electron beam Lithography equipment. The patterned silicon wafer is developed with MIBK: IPA for 60 seconds and washed with IPA for another 60 s and then dried with Nitrogen gas. Following this step, an approximate of 15 nm thickness of Titanium is layered on top of the patterned silicon substrate as Titanium improves the adhesion of gold on Silicon. Around 95 nm thickness of Gold is deposited on top of the Titanium coated Silicon substrate by high vacuum evaporator (Kurt J. Lesker PVD-75 Evaporator). After the metal depositions, the lift-off process is performed by removing the positive tone photo resist by cleaning the substrate in acetone ultrasonic bath for 3 mins and then followed by rinsing with Isopropenol and de-ionized water in order to prevent redeposition.

Figure 29:
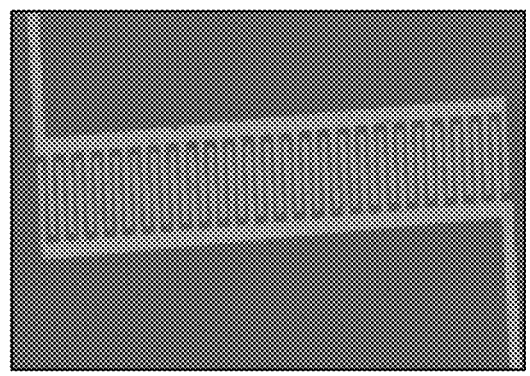
FIG. 29 is a microscopic image of interdigitated electrodes.

FIG. 29 shows the microscopic image of the patterned interdigitated electrodes.

The interdigitated nanoelectrodes were cleaned multiple times with ethanol and de-ionized water before addition of other chemical layers. The sensor surface was coated with Self Assembled Monolayer (SAM) by incubating the sensor in 50 mM solution of Thiourea overnight followed by rinsing with ethanol and de-ionized water. The formation of the SAM layer was confirmed using two point electrical probe station. The CNTs were placed on top of the modified sensor with SAM layer.

Figure 30:
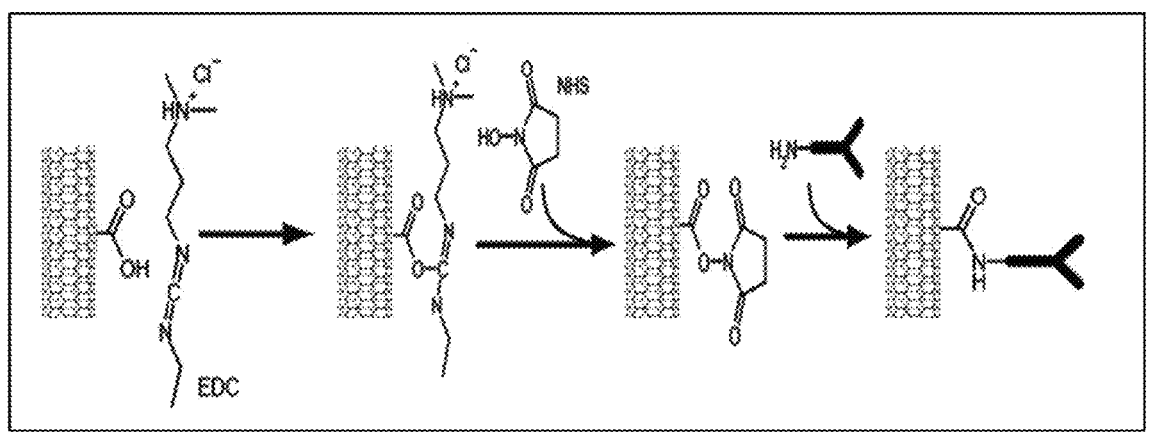
FIG. 30 is an illustration of a surface activation process of the carboxy CNT for antibody binding.

The surface of the CNTs having a carboxylic functionalized group was activated using 50 mM concentration of EDC and NHS for approximately 4 hours. The surface activation of the functionalized carbon nanotubes enables it to bind with the antibodies covalently [22]. Surface activation mechanism is shown in FIG. 30.

Immobilization of the Antibodies

The sensor surface was washed using PBS solution before the immobilization of the antibodies. Followed by this step, the immobilization of the antibodies was done by incubating the modified sensor with 0.5 µl of 7 mg/ml CA-125 antibodies in PBS for 2 hours. The incubation process was done at 4° C. The sensor surface was rinsed using PBS solution and approximately 1 µl of ethanolamine was added on top of the modified sensor for 1 h to block the non-reacted groups on the sensor surface. The sensor was then cleaned with PBS and dried with nitrogen gas.

Addition of the Antigen

Figure 31A:
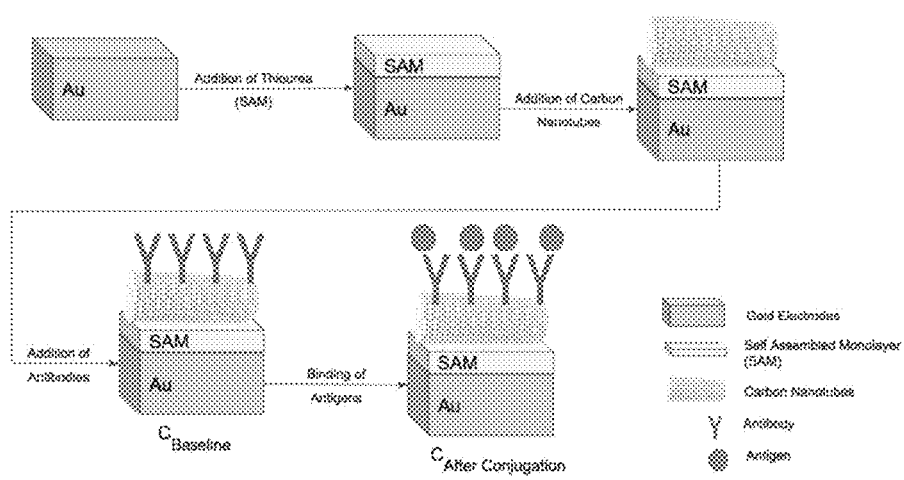
FIG. 31A is a flow diagram of various layer formations on top of the sensor.
Figure 31B:
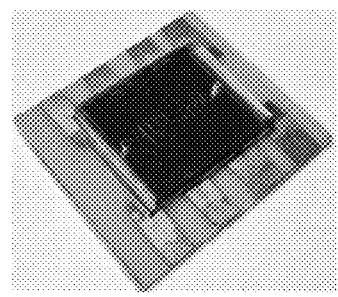
FIG. 31B is a photographic image of one embodiment of the biosensor.

The biosensor is integrated with the PDMS microfluidic channel on top through which the antigens solutions are meant to be passed. A drop of CA-125 antigens solution (5 µL) having 560 µg/ml concentration is placed on the inlet of the hydrophilic PDMS channel. The antigens solution flows through the microfluidic channel due to capillary effect and interacts with the antibodies, which are exposed on top of the sensor platform. The schematic model of the biosensor is shown in FIGS. 31A-31B.

Measurement of Capacitance

The capacitance is measured at all the stages having different layers. All the measurement were taken using two point probe station and the dielectric parameters were calculated by using Agilent 4284A Precision LCR meter.

Figure 32:
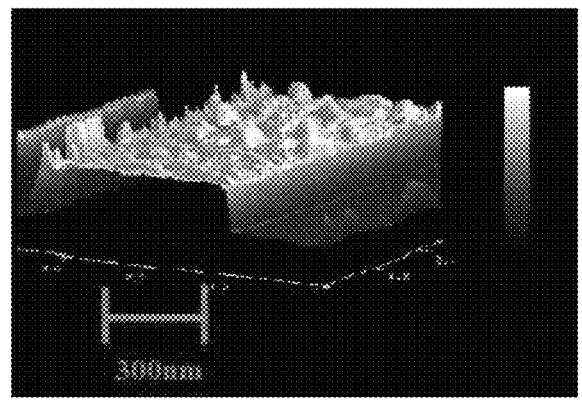
FIG. 32 is an AFM image of the interdigitated gold electrode coated with SAM layer.

FIG. 32 shows the probe station used in this experiment for capacitive measurements. The scanned frequency was in the range between 10 kHz and 100 kHz with a step of 10 khz at each succession. The capacitance was calculated for (a) bare electrodes, (b) insulation of the electrodes by SAM layer; (c) after addition of carboxylic functionalized Carbon Nanotubes, (d) after immobilization of the CA-125 antibodies and (e) after conjugation of CA-125 antigens and antibodies. All the measurements were taken at 100 mV amplitude with the DC voltage at 0.5V.

Figure 33:
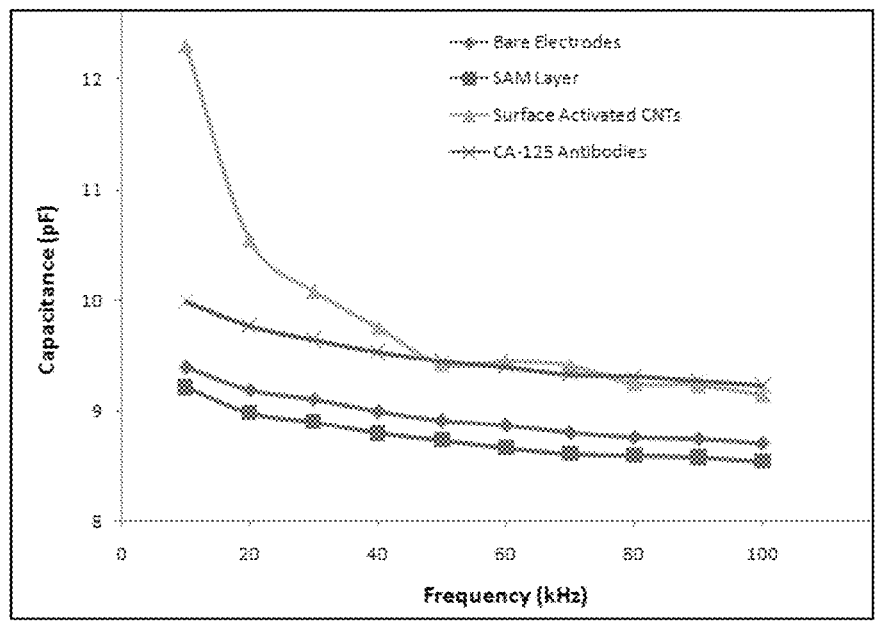
FIG. 33 is a graph illustrating capacitance versus frequency plot for different layers on top of sensor.
Figure 34:
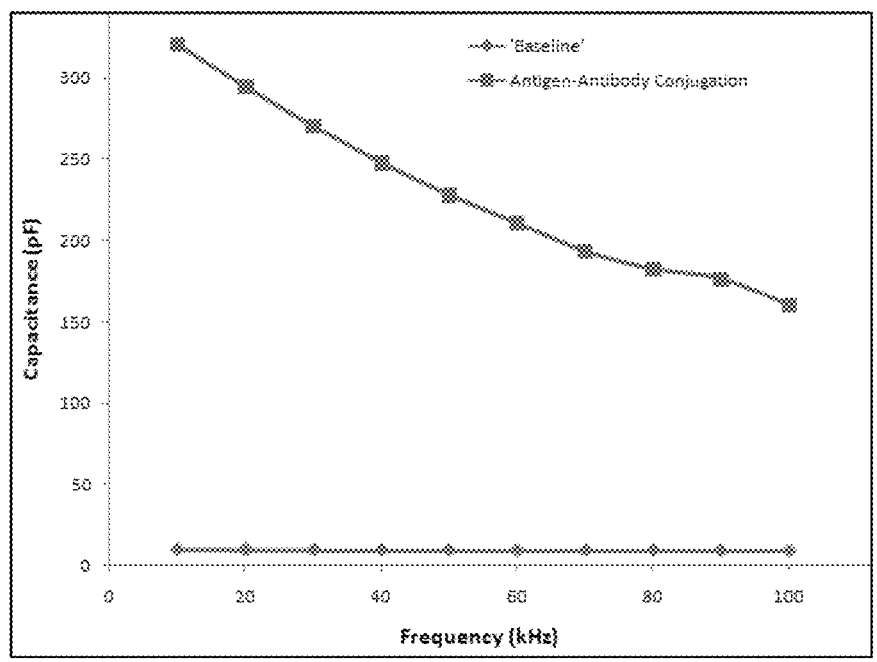
FIG. 34 is a graph illustrating capacitance versus frequency plot for the baseline and after Ag-Ab conjugation.

FIG. 33 illustrates capacitance versus frequency plot for different layers on top of sensor. FIG. 34 shows the plot between capacitance and frequency at 0.5V for the different stages.

Results

Interdigitated Electrodes

The interdigitated electrodes are designed for capacitive measurements. The advantage of using interdigitated electrodes is to increase the effective net surface area of the capacitive measurements within the same volume or space. The interdigitated electrodes work in a similar way to that of the conventional parallel plate capacitor. The dielectric properties of the medium between the parallel plates provide the electrical information such as conductivity, permittivity, capacitance, and impedance. The interdigitated electrodes produce the electric field lines which penetrate the medium and depending on the geometry and configuration of the electrodes, the electric field can penetrate deeper and wider. The capacitance of the interdigitated electrodes is defined as $$C = \varepsilon \, \varepsilon_o \left( \frac{A}{d} \right)$$

where $\varepsilon$ is the dielectric constant between the plates and $\varepsilon_0$ (8.85 pF/m) is the constant of permittivity of the free space, A is the area of the electrodes and d is the distance between the parallel electrodes.

Formation of SAM

The formation of the SAM layer was confirmed by AFM image of the electrodes. The purpose of the SAM layer is to insulate the electrodes to prevent the electrodes from short circuiting.

FIG. 33 shows the AFM image of the electrodes. The increase in the height of the electrodes and roughness at the surface confirm the formation of the SAM layer. The capacitive measurements, in addition to the AFM image, confirm the SAM layer insulation on top of the electrodes.

Capacitance Measurements at Different Layers

The dielectric permittivity of the SAM layer is lower than that of bare electrodes due to which the capacitance is slightly lower to the bare electrodes. FIG. 34 shows the lower capacitance curve of the SAM layer compared to the bare electrodes. The carbon nanotubes exhibit excellent electrical, chemical and structural properties that makes them highly promising for nanoscale sensing.

The carbon nanotubes having better permittivity resulted in higher capacitance to that of both bare electrodes and the SAM layer. The carbon nanotube having around 3% surface coverage of carboxylic functionalized group was used for the experiment which would covalently bind the antibodies to the carbon nanotubes. Due to the lack of sufficient coverage of the carboxylic group on CNTs, the concentration of the immobilized antibodies on top of CNT based sensor is low compared to other nanoparticles based biosensor platform. As a result, the capacitance curve of the immobilized CA-125 antibodies is similar to surface activated CNTs except at the lower frequencies. This curve is also regarded the 'Baseline' as considering this as the baseline, the capacitance of the antigen-antibody [Ag-Ab] conjugation is measured.

Capacitance Measurements Before and after Ab-Ag Conjugation

The antigens and the antibodies interaction are highly specific and selective. The specific antigens and antibodies interaction increases the net molecular size due to its complex formation. The change in the size of the complex will disturb or interfere with the distribution of the charges present in the dielectric medium. The antigens binding to the antibodies directly affect the distribution of charges in dielectric interface, which results in dipole moment. The dipole-dipole interaction stimulates the polarization in the dielectric interface. As a result, the dielectric property of each antigen complex over the range of frequencies has its unique variation which is measured to check the significant changes. With this phenomenon, the measured capacitance or impedance of the sensor varies with the relative changes in dielectric properties on sensor surface.

Figure 35:
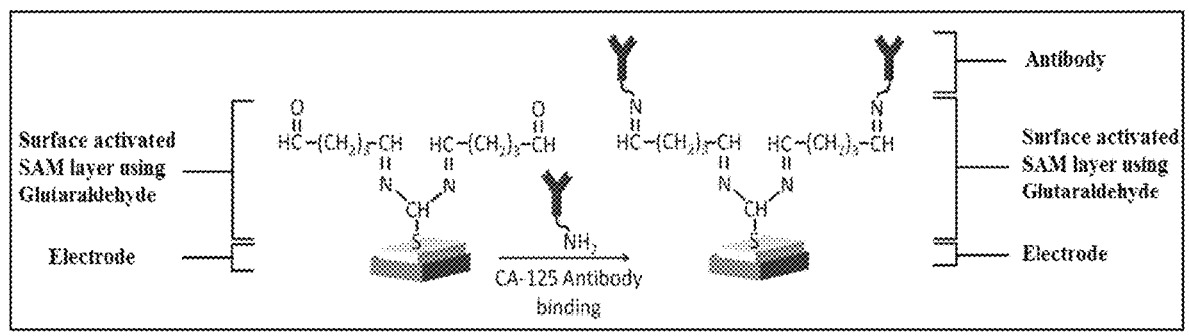
FIG. 35 is an illustration of a surface activation mechanism of non-CNTs based biosensor using glutaraldehyde.

FIG. 35 shows the plot between the capacitance and frequency of the 'Baseline' and 'after the antigen-antibody conjugation'.

When the antigens solution is passed through the microfluidic channel, the interaction between the antigens and the antibodies takes place, which results in the change of dielectric properties of the medium over the sensor surface. The change in the dielectric properties directly influences the change in the capacitance over a range of frequency. The highest capacitance values are observed at 10 kHz for both Baseline and after Ag-Ab conjugation in the selected frequency range. The capacitance of the 'Baseline is around 10 pF and is increased to a value around 321 pF after the antigens interaction. The significant change is the capacitance values represent the conjugation of the CA-125 antigens and antibodies. The plot also demonstrates the functionality of the CNTs based interdigitated electrodes biosensor.

Capacitance Comparison Between CNT and Non-CNT Based Biosensor

The CNT based biosensor is compared with the non-CNT based biosensors for checking the enhancement in sensitivity. The non-CNT based biosensor consists of antibodies immobilized on top of the SAM layer using Glutaraldehyde. The Thiourea layer on top of gold electrodes is surface activated using Glutaraldehyde. As a result, the antibodies are bound to the modified Thiourea layer.

Figure 36:
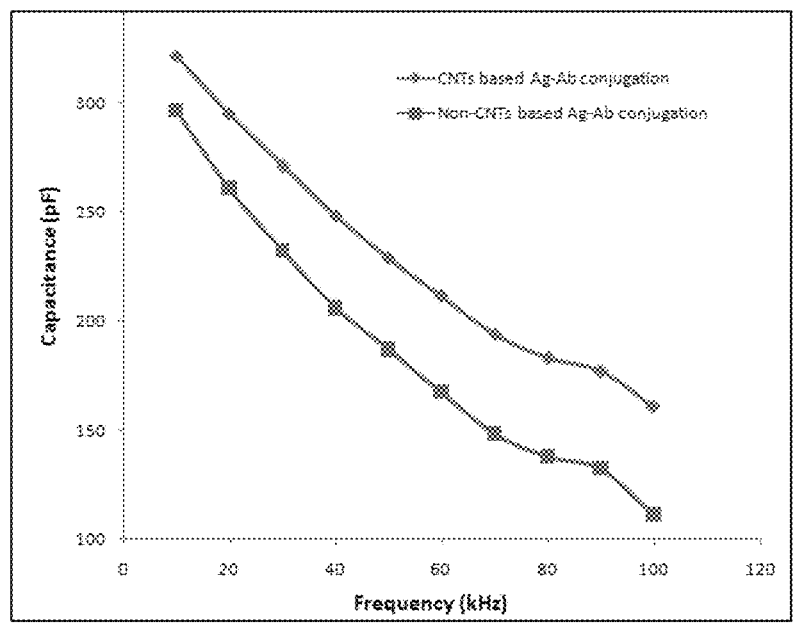
FIG. 36 is a graph illustrating Ag-Ab conjugation capacitance comparison between CNTs and Non-CNTs based biosensor.
Figure 37:
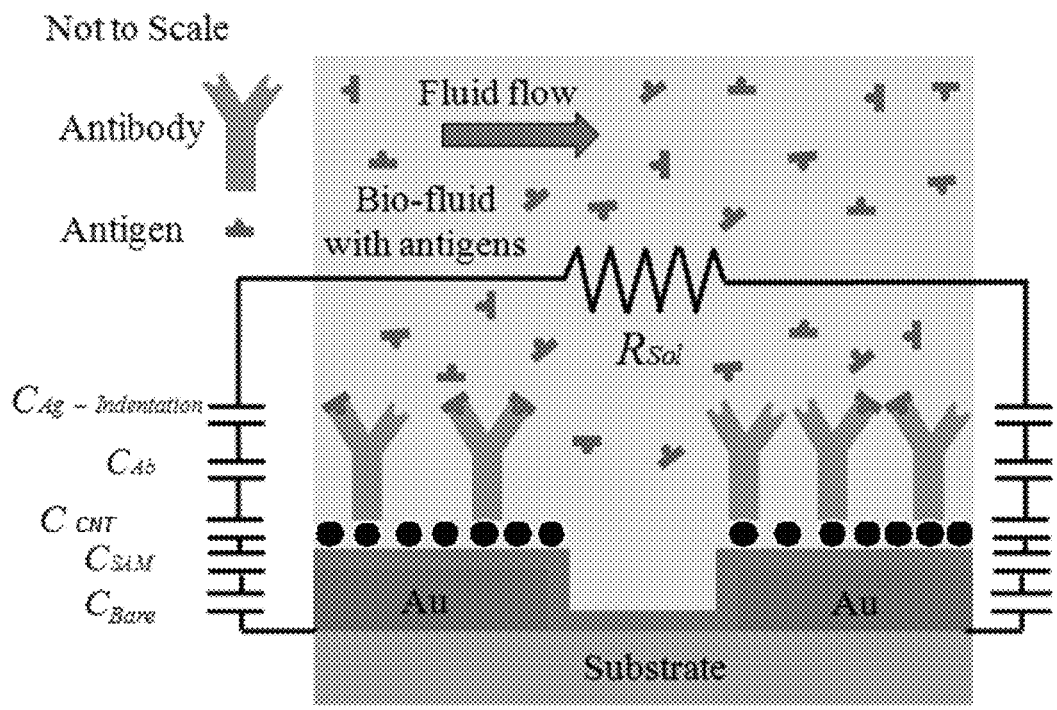
FIG. 37 is a schematic diagram showing one embodiment of a carbon nanotube (CNT) based biosensor.

FIG. 36 shows the surface activation mechanism of the non-CNTs based sensing platform. The plot shows the capacitive measurements comparison between CNT based and non-CNT based biosensor after the antigen-antibody conjugation. The capacitance curve with the CNTs shows significantly higher capacitive values compared to the non-CNTs based biosensor. Both capacitive curves were measured between 10 kHz to 100 kHz frequency at 0.5V and 100 mV amplitude. The lowest capacitive difference between CNT and non-CNT based biosensors were recorded to be at 10 kHz with the values of 321.06 pF and 296 pF respectively. The significant difference in the values of the capacitance was observed at 100 kHz. The difference between the two curves is increasing with frequency as shown in FIG. 37.

As the frequency increases, the polarity of the interdigitated electrodes increases significantly making the capacitance unstable and lower. The CNT based biosensor showed the capacitance value of approximately 160 pF and the non-CNT based ones around 111 pF at 100 kHz. Since the CNTs and the antibodies have better dielectric permittivity, the capacitance of the sensing platform shows significantly higher capacitance values compared to the non-CNTs based biosensor. The higher capacitive values of the CNT based biosensor depict its sensitivity enhancement over the non-CNT based biosensor. The potential reason for the enhancement is the higher number of the antibodies on top of the sensor surface as CNTs provides high surface to volume ratio.

Figure 38:
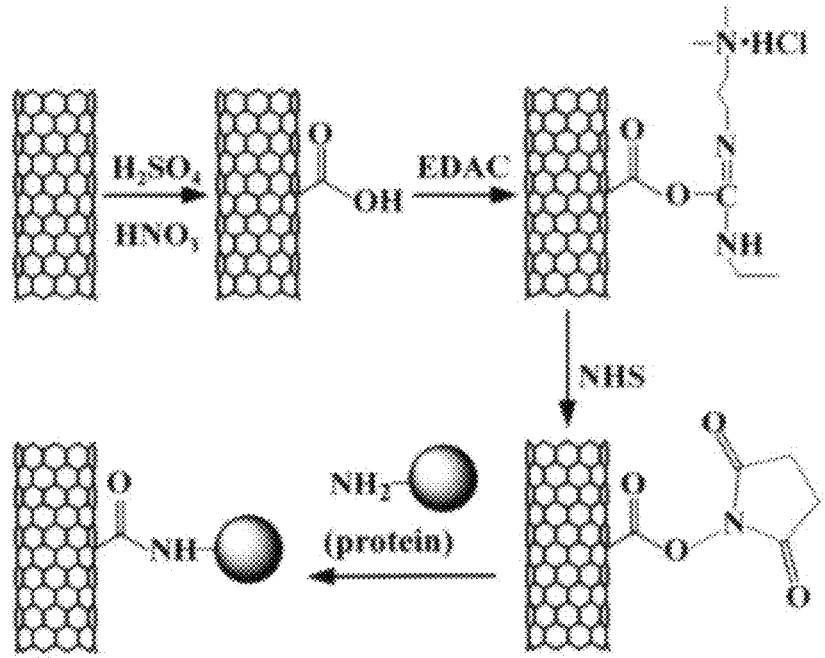
FIG. 38 is a graphic illustration showing addition of a functional group and surface activation.

As a result, significantly more number of antibodies is present for the antigens conjugation. Another good aspect is the covalent bonding between the CNTs and the antibodies due to carboxylic functionalized group present on top of CNTs which persisted even under the shear flow rate conditions. The covalent bonding prevented the CA-125 antibodies from getting washed on the sensor surface which resulted in presence of more antibodies comparatively for successful binding. Again, the invention also functions and utilizes one or more of the following features as shown in the below examples and below detailed description. Disclosed as shown in FIG. 38 is a graphic illustration showing addition of a functional group and surface activation.

Figure 41A:
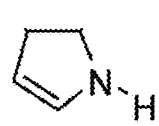
FIGS. 41A-41D illustrate additional functional group and surface activation on graphene, four nitrogen functional groups in N-G, 41A pyrrolic N (N_H), 41B pyridinic N, 41C graphitic N, and 41D pyridinic-N oxide.
Figure 41B:
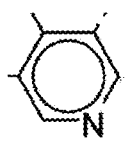
Figure 41C:
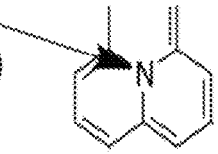
Figure 41D:

FIGS. 39A-39D illustrates additional carbon-based nanomaterials for nano electrodes. For example, FIG. 39A is graphene, FIG. 39B is graphite, FIG. 39C is a carbon nanotube, and FIG. 39D is fullerene. FIGS. 40A-40B illustrate additional carbon based nanomaterials for nano-electrodes and FIGS. 41A-41D illustrate additional functional group and surface activation on graphene, four nitrogen functional groups in N-G. As illustrated in FIGS. 41A-41D shown are FIG. 41A pyrrolic N (N_H); FIG. 41B pyridinic N; FIG. 41C graphitic N; and FIG. 41D pyridinic-N oxide.

CONCLUSION

In summary, a functional CNTs based biosensor with interdigitated electrodes pattern and integrated microfluidic channel was developed with significant improvements and advancements over the current state of the art devices. The interdigitated electrodes supported the sensing mechanism at minimal space and even at lower concentration of the CA-125 antigens. The carbon nanotubes showed higher capacitance values that directly influenced the enhancement of the sensitivity of the sensor due to their high surface to volume ratio and better electron transfer rate. The CA-125 antibodies are bonded covalently with the CNTs, which provided more stability of the antibodies even under shear flow rate conditions. The experiments in these examples used 3% surface coverage of carboxylic functionalized CNTs. However, depending on the embodiments, additional surface coverage may be possible. The increased percentage of the carboxylic functionalized group on the surface of the CNTs may provide a platform to attach more antibodies which would directly influence the stability and sensitivity. The CNTs based interdigitated electrodes biosensor may serve as a promising platform for the other disease biomarkers for detection purposes.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A microfluidic chip with enhanced sensitivity to successfully detect the disease-specific antigen, comprising
    a biochip having a multichannel distribution of a plurality of hydrophilic microchannels from a single inlet, wherein each of the plurality of hydrophilic microchannels provides a controlled self-driven flow of a biofluid sample selected from a group consisting of blood, urine, and sputum, wherein the biochip performs detection of a disease-specific antigen when the biofluid is in motion in the microchannel and the biofluid is self-driven in the microchannel using capillary action;
    a multiple gold nano interdigitated electrodes (IDE) for capacitive sensing with an enhanced sensitivity achieved by using a plurality of chemically coated nanoparticles to bond a plurality of cancer antibodies to a surface of the electrode and incorporating a multiple sensing platform on different hydrophilic microchannels with the same plurality of cancer antibodies in the microchannel;

the multiple gold nano IDE incorporated at different sections of the microchannel to sense biological interactions;

a circuit fabricated on a surface of the microchannel to detect biomolecular interactions in the microchannel, wherein the circuit includes the gold nano interdigitated electrode;

the plurality of cancer antibodies are coated in different hydrophilic microchannels and on a plurality of surface-activated, self-assembled monolayer (SAM) on the surface of the gold nano interdigitated electrode, the cancer antibody is capable of antigen/antibody conjugation with CA-125 ovarian cancer antigen or Human Epididymis Protein 4 (HE-4), wherein the sample has a cancer antigen that forms an antigen/antibody conjugation that is detected via a change in a capacitance of the circuit in the biochip, and the change in the capacitance is due to the cancer antigens in the sample and assists to determine an existence of a cancer, wherein the multichannel distribution improves detection of multiple antigens, by using the plurality of antibodies coated in different channels and different sections of the microchannel for the enhanced sensitivity of the biochip, as compared to detection not using the plurality of antibodies coated in different channels;

wherein, a plurality of nanoparticles disposed onto the SAM layer and having the antibody disposed onto the nanoparticles allows the antibody to adhere more readily on the surface of the electrodes, as compared to antibody adhesion without nanoparticles, further for the enhanced sensitivity of the biochip sensitivity to detect a stage of ovarian cancer including stage 1A or stage 1B by the biochip; and when the sample is in motion in the microchannel without external force and the sample contains, CA-125, and Human Epididymis Protein 4 (HE-4) concentrations in pico ($1 \times 10^{-12}$) and femto ($1 \times 10^{-15}$) scale size level concentrations, a stage of ovarian cancer including stage 1A or stage 1B is detected by the biochip in a patient for physicians to schedule the patient for a next level of cancer diagnosis to confirm the stage of ovarian cancer.

2. The microfluidic chip of claim 1 wherein, biofluid sample flow in the microchannel is self-driven due to the capillary effect of biofluid in the hydrophilic microchannel.

3. The microfluidic chip of claim 1, wherein the microchannel is surface treated with oxygen plasma for a duration up to 100 seconds to control hydrophilicity of a microchannel surface for controlling flow rate of biofluid in the microchannel.

4. The microfluidic chip of claim 1, wherein the nanoparticles form an intermediate layer to enhance the binding capability of the antibody to the nano electrodes for enhanced sensitivity and wherein the controlled self-driven flow in the microchannel is controlled by a surface treatment on a microchannel surface.

5. The microfluidic chip of claim 1, wherein the controlled self-driven flow rate in the microchannel provides necessary conditions for biological reactions including an antigen-antibody complex formation.

6. The microfluidic chip of claim 1, wherein the biochip is incorporated into a point of care device connected to a computer using USB.

7. The microfluidic chip of claim 1, wherein the biochip is incorporated into a point of care device connected to a wireless device as IOT.

8. The microfluidic chip of claim 1, wherein the biochip is incorporated into a point of care device connected to a computer using USB supported with software to display results on a laptop to which the USB is connected.

9. The microfluidic chip of claim 1, wherein the biochip is incorporated into a point of care device connected to a wireless device as IOT supported with software to display results in a wireless device.

10. A microfluidic chip with enhanced sensitivity, comprising
a nano circuit having at least one interdigitated nano electrode;
a hydrophilic microchannel for a biofluid sample to flow therethrough, the biofluid selected from a group consisting of blood, urine, and sputum;
at least one self-assembled monolayer (SAM) layer covering the electrode;
an antibody disposed about the electrode for detection of an antigen;
wherein an antigen/antibody conjugation is detected by capacitance change in the nanocircuit, and the biofluid sample flows in the microchannel and is a controlled self-driven flow due to a controlled capillary effect of the biofluid in the microchannel with a controlled hydrophilicity;
a plurality of nanoparticles disposed about the SAM layer; and wherein the antibody is disposed onto the nanoparticles to allow the antibody to adhere more readily on a surface of the electrodes as compared to antibody adhesion without nanoparticles; and wherein the nanoparticles are selected from a group consisting of a metallic material, a gold (Au) material, a silver (Ag) material, a non-metallic carbon material, a carbon nanotube (CNT), a graphene, an active carbon, and any combination thereof; and
when the sample is in motion in the microchannel without external force and the sample contains specific cancer biomarkers CA-125 and Human Epididymis Protein 4(HE04) in pico ($1 \times 10^{-12}$) and femto ($1 \times 10^{-15}$) scale level concentrations, a stage of ovarian cancer including stage 1A or 1B is detected by the biochip in a patient for physicians to schedule the patient for a next level of cancer diagnosis to confirm the stage of ovarian cancer.

11. The microfluidic chip of claim 10, wherein the interdigitated nano electrode contains gold (Ag).

12. The microfluidic chip of claim 10, wherein the antibody is immobilized on a surface of the nanoparticles deposited in a top of the SAM layer.

13. The microfluidic chip of claim 10, wherein the self-driven flow in the microchannel is controlled by the surface treatments on a microchannel surface.

14. The microfluidic chip of claim 10, wherein a controlled flow rate in the microchannel provides for a biological reaction.

15. The microfluidic chip of claim 10, wherein the biological reaction is an antigen-antibody complex formation.

16. The microfluidic chip of claim 10, further including nanoparticles disposed on the SAM layer, wherein the nanoparticles have a more sensitive change of a capacitance value, as compared to not using the nanoparticles, that directly influences enhancement of sensitivity of the biosensor due to a high surface to volume ratio of the nanoparticles and better electron transfer rate as compared to without the nanoparticles on the SAM layer.

17. The microfluidic chip of claim 16, wherein the antibody is bonded covalently with the nanoparticles to provide stability of the antibody under shear flow rate conditions from the self driven flow of the biofluid sample.

18. The microfluidic chip of claim 16, wherein an increased percentage of a carboxylic functionalized group on a surface of the nanoparticles provides a platform to attach antibodies and directly influence stability and sensitivity of the antibody.

19. The microfluidic chip of claim 16, wherein the interdigitated electrodes are used as a platform for various disease biomarkers for detection of various diseases.

* * * * *